(12) United States Patent
Weitzel et al.

(10) Patent No.: US 10,517,569 B2
(45) Date of Patent: Dec. 31, 2019

(54) LINEAR MAGNETIC DRIVE TRANSDUCER FOR ULTRASOUND IMAGING

(71) Applicant: THE REGENTS OF THE UNIVERSITY OF MICHIGAN, Ann Arbor, MI (US)

(72) Inventors: William Weitzel, Ypsilanti, MI (US); Grant Kruger, Ann Arbor, MI (US); Brian Thelen, Ann Arbor, MI (US); Jonathan Rubin, Ann Arbor, MI (US); Leo Koziol, Canton, MI (US); Robert Brook, Canton, MI (US); Mainak Mitra, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 638 days.

(21) Appl. No.: 13/890,906

(22) Filed: May 9, 2013

(65) Prior Publication Data
US 2013/0345566 A1 Dec. 26, 2013

Related U.S. Application Data

(60) Provisional application No. 61/645,025, filed on May 9, 2012.

(51) Int. Cl.
*A61B 8/00* (2006.01)
*A61B 8/08* (2006.01)
(Continued)

(52) U.S. Cl.
CPC .......... *A61B 8/4483* (2013.01); *A61B 8/0891* (2013.01); *A61B 8/4427* (2013.01);
(Continued)

(58) Field of Classification Search
CPC ... A61B 8/0891; A61B 8/4427; A61B 8/4461; A61B 8/4472; A61B 8/4483;
(Continued)

(56) References Cited

U.S. PATENT DOCUMENTS 3,964,296 A * 6/1976 Matzuk .................... A61B 8/00
73/607
4,275,597 A 6/1981 Quedens et al.
(Continued)

OTHER PUBLICATIONS

Nippon Pulse America, "S040 Linear Shaft Motor for Small-Scale High Precision", Aug. 9, 2011, Nippon Pulse website.*
(Continued)

*Primary Examiner* — Michael T Rozanski
(74) *Attorney, Agent, or Firm* — Marshall, Gerstein & Borun LLP

(57) ABSTRACT

An ultrasound imaging system uses a magnetic linear motor driven ultrasound scanner, with accurate track and hold operation and/or other motion feedback, to scan a two dimensional or three dimensional area of a sample. The scanner is implemented in a low-power and low-bandwidth handheld device and is connected with a remote image processing system that receives raw data and performs full ultrasound image analysis and creation, allowing the handheld to be used for scanning, pre-processing, and display.

33 Claims, 28 Drawing Sheets

(51) Int. Cl.
*G01S 15/89* (2006.01)
*G01N 29/22* (2006.01)
*G01S 7/00* (2006.01)
*G01S 7/52* (2006.01)

(52) U.S. Cl.
CPC .......... *A61B 8/4461* (2013.01); *A61B 8/4472* (2013.01); *A61B 8/461* (2013.01); *A61B 8/488* (2013.01); *G01N 29/222* (2013.01); *G01S 15/8945* (2013.01); *A61B 8/483* (2013.01); *A61B 8/56* (2013.01); *G01S 7/003* (2013.01); *G01S 7/52042* (2013.01); *G01S 7/52065* (2013.01); *G01S 15/8915* (2013.01); *G01S 15/8995* (2013.01)

(58) Field of Classification Search
CPC ......... A61B 8/461; A61B 8/483; A61B 8/488; A61B 8/56; G01N 29/222; G01S 15/8915; G01S 15/8945; G01S 15/8995; G01S 7/003; G01S 7/52042; G01S 7/52065
USPC .................................................. 600/443, 445
See application file for complete search history.

(56) References Cited

U.S. PATENT DOCUMENTS

| | | | |
|---|---|---|---|
| 4,407,293 A | 10/1983 | Suarez, Jr. et al. | |
| 4,457,311 A | 7/1984 | Sorenson et al. | |
| 4,802,487 A | 2/1989 | Martin et al. | |
| 4,858,613 A | 8/1989 | Fry et al. | |
| 4,882,934 A | 11/1989 | Leffert et al. | |
| 4,917,096 A | 4/1990 | Englehart et al. | |
| 4,955,365 A | 9/1990 | Fry et al. | |
| 4,974,211 A | 11/1990 | Corl | |
| 5,003,238 A | 3/1991 | Lum et al. | |
| 5,036,855 A | 8/1991 | Fry et al. | |
| 5,159,931 A | 11/1992 | Pini | |
| 5,178,150 A | 1/1993 | Silverstein et al. | |
| 5,181,514 A | 1/1993 | Solomon et al. | |
| 5,211,176 A | 5/1993 | Ishiguro et al. | |
| 5,353,796 A | 10/1994 | Schroeder et al. | |
| 5,361,768 A | 11/1994 | Webler et al. | |
| 5,400,790 A | 3/1995 | Pohan et al. | |
| 5,465,724 A | 11/1995 | Sliwa, Jr. et al. | |
| 5,469,852 A | 11/1995 | Nakamura et al. | |
| 5,485,846 A | 1/1996 | Webler et al. | |
| 5,562,096 A | 10/1996 | Hossack et al. | |
| 5,572,448 A | 11/1996 | Judell | |
| 5,592,942 A | 1/1997 | Webler et al. | |
| 5,603,326 A | 2/1997 | Richter | |
| 5,605,154 A | 2/1997 | Ries et al. | |
| 5,630,417 A | 5/1997 | Petersen et al. | |
| 5,704,898 A | 1/1998 | Kokish | |
| 5,720,285 A | 2/1998 | Petersen | |
| 5,722,412 A | 3/1998 | Pflugrath et al. | |
| 5,755,571 A | 5/1998 | Companion | |
| 5,759,153 A | 6/1998 | Webler et al. | |
| 5,820,564 A | 10/1998 | Slayton et al. | |
| 5,836,880 A | 11/1998 | Pratt | |
| 5,848,969 A | 12/1998 | Panescu et al. | |
| 5,904,651 A | 5/1999 | Swanson et al. | |
| 5,908,445 A | 6/1999 | Whayne et al. | |
| 5,967,984 A | 10/1999 | Chu et al. | |
| 5,983,123 A | 11/1999 | Shmulewitz | |
| 5,999,167 A | 12/1999 | Marsh et al. | |
| 6,004,272 A | 12/1999 | Barry et al. | |
| 6,036,646 A | 3/2000 | Barthe et al. | |
| 6,049,159 A | 4/2000 | Barthe et al. | |
| 6,050,943 A | 4/2000 | Slayton et al. | |
| 6,099,474 A | 8/2000 | Solek | |
| 6,108,439 A | 8/2000 | Ishiguro | |
| 6,110,121 A | 8/2000 | Lenker | |
| 6,117,101 A | 9/2000 | Diederich et al. | |
| 6,120,452 A | 9/2000 | Barthe et al. | |
| 6,126,600 A | 10/2000 | Oxaal et al. | |
| 6,139,500 A | 10/2000 | Clark | |
| 6,167,765 B1 | 1/2001 | Weitzel | |
| 6,186,864 B1 | 2/2001 | Fisher, Jr. et al. | |
| 6,213,948 B1 | 4/2001 | Barthe et al. | |
| 6,409,669 B1 | 6/2002 | Hager et al. | |
| 6,409,672 B2 | 6/2002 | Webler et al. | |
| 6,425,870 B1 | 7/2002 | Flesch | |
| 6,440,071 B1 | 8/2002 | Slayton et al. | |
| 6,500,121 B1 | 12/2002 | Slayton et al. | |
| 6,527,731 B2 | 3/2003 | Weiss et al. | |
| 6,540,679 B2 | 4/2003 | Slayton et al. | |
| 6,540,681 B1* | 4/2003 | Cheng .................. | A61B 8/0866 600/443 |
| 6,561,982 B2 | 5/2003 | Greppi et al. | |
| 6,572,548 B2 | 6/2003 | Cerofolini | |
| 6,574,499 B1 | 6/2003 | Dines et al. | |
| 6,575,927 B1 | 6/2003 | Weitzel et al. | |
| 6,582,381 B1 | 6/2003 | Yehezkeli et al. | |
| 6,585,666 B2 | 7/2003 | Suh et al. | |
| 6,589,174 B1 | 7/2003 | Chopra et al. | |
| 6,592,520 B1 | 7/2003 | Peszynski et al. | |
| 6,613,005 B1 | 9/2003 | Friedman et al. | |
| 6,623,430 B1 | 9/2003 | Slayton et al. | |
| 6,623,433 B2 | 9/2003 | Webler et al. | |
| 6,659,955 B1 | 12/2003 | Marian, Jr. | |
| 6,679,845 B2 | 1/2004 | Ritter et al. | |
| 6,709,414 B2 | 3/2004 | Weitzel et al. | |
| 6,776,758 B2 | 8/2004 | Peszynski et al. | |
| 6,780,153 B2 | 8/2004 | Angelsen et al. | |
| 6,872,180 B2 | 3/2005 | Reinhardt et al. | |
| 6,996,432 B2 | 2/2006 | Ostrovsky et al. | |
| 7,022,080 B2 | 4/2006 | Marian, Jr. | |
| 7,100,449 B2 | 9/2006 | Busch et al. | |
| 7,142,905 B2 | 11/2006 | Slayton et al. | |
| 7,214,230 B2 | 5/2007 | Brock et al. | |
| 7,229,411 B2 | 6/2007 | Slayton et al. | |
| 7,302,851 B2 | 12/2007 | Czerw et al. | |
| 7,359,691 B2 | 4/2008 | Adachi et al. | |
| 7,393,325 B2 | 7/2008 | Barthe et al. | |
| 7,484,412 B2 | 2/2009 | Hart et al. | |
| 7,491,172 B2 | 2/2009 | Bruestle | |
| 7,494,469 B2 | 2/2009 | Bruestle | |
| 7,497,120 B2 | 3/2009 | Schneider et al. | |
| 7,524,289 B2 | 4/2009 | Lenker | |
| 7,530,271 B2 | 5/2009 | Busch et al. | |
| 7,530,958 B2 | 5/2009 | Slayton et al. | |
| 7,554,026 B2 | 6/2009 | de Moraes | |
| 7,568,391 B2 | 8/2009 | Schneider et al. | |
| 7,569,015 B2 | 8/2009 | Donaldson et al. | |
| 7,571,336 B2 | 8/2009 | Barthe et al. | |
| 7,572,223 B2 | 8/2009 | Donaldson | |
| 7,580,762 B2 | 8/2009 | Abrams et al. | |
| 7,591,787 B2 | 9/2009 | Tortoli | |
| 7,652,259 B2 | 1/2010 | Kimchy et al. | |
| 7,666,143 B2 | 2/2010 | Wilser et al. | |
| 7,678,056 B2 | 3/2010 | Wilser et al. | |
| 7,691,060 B2 | 4/2010 | Angelsen et al. | |
| 7,727,152 B2 | 6/2010 | Qin et al. | |
| 7,740,587 B2 | 6/2010 | Hiltawsky | |
| 7,771,360 B2 | 8/2010 | Johnson et al. | |
| 7,781,973 B2 | 8/2010 | Miyake et al. | |
| 7,801,591 B1 | 9/2010 | Shusterman | |
| 7,824,348 B2 | 11/2010 | Barthe et al. | |
| 7,914,452 B2 | 3/2011 | Hartley et al. | |
| 7,914,453 B2 | 3/2011 | Slayton et al. | |
| 7,931,594 B2 | 4/2011 | Hirsh | |
| 7,987,303 B2 | 7/2011 | Bartlett | |
| 7,989,177 B2 | 8/2011 | Bystryak et al. | |
| 8,038,619 B2 | 10/2011 | Steinbacher | |
| 8,038,622 B2 | 10/2011 | Abraham | |
| 8,052,609 B2 | 11/2011 | Harhen | |
| 8,057,395 B2 | 11/2011 | Lenker | |
| 8,057,397 B2 | 11/2011 | Li et al. | |
| 8,070,685 B2 | 12/2011 | Harhen et al. | |
| 8,090,065 B2 | 1/2012 | Gabrielson et al. | |
| 8,147,413 B2 | 4/2012 | Abraham | |
| 8,147,414 B2 | 4/2012 | Abraham | |

(56) References Cited

U.S. PATENT DOCUMENTS

| | | |
|---|---|---|
| 8,157,741 B2 | 4/2012 | Hirota |
| 8,166,332 B2 | 4/2012 | Barthe et al. |
| 8,211,025 B2 | 7/2012 | Donaldson et al. |
| 8,220,334 B2 | 7/2012 | Klessel et al. |
| 8,235,903 B2 | 8/2012 | Abraham |
| 8,235,909 B2 | 8/2012 | Barthe et al. |
| 8,312,771 B2 | 11/2012 | Randall et al. |
| 8,317,711 B2 | 11/2012 | Dala-Krishna |
| 8,323,199 B2 | 12/2012 | Salcudean et al. |
| 8,356,518 B2 | 1/2013 | Alleyne et al. |
| 8,382,671 B2 | 2/2013 | Anthony et al. |
| 8,409,097 B2 | 4/2013 | Slayton et al. |
| 8,409,102 B2 | 4/2013 | Griffin et al. |
| 2001/0020126 A1 | 9/2001 | Swanson et al. |
| 2001/0029328 A1 | 10/2001 | Crowley |
| 2002/0016545 A1 | 2/2002 | Quistgaard et al. |
| 2002/0099356 A1 | 7/2002 | Unger et al. |
| 2002/0103432 A1 | 8/2002 | Kawchuk |
| 2002/0111548 A1 | 8/2002 | Swanson et al. |
| 2002/0117904 A1* | 8/2002 | Godkin .............. H02K 41/0356 310/12.24 |
| 2003/0011362 A1 | 1/2003 | Gohlsch et al. |
| 2003/0045815 A1 | 3/2003 | Ombrellaro |
| 2003/0055338 A1 | 3/2003 | Steininger et al. |
| 2003/0095692 A1 | 5/2003 | Mundy et al. |
| 2003/0135135 A1* | 7/2003 | Miwa ...................... A61N 7/00 601/2 |
| 2003/0167004 A1* | 9/2003 | Dines ................... A61B 6/0414 600/437 |
| 2003/0195510 A1 | 10/2003 | Schaer |
| 2004/0073118 A1 | 4/2004 | Peszynski et al. |
| 2004/0097836 A1 | 5/2004 | Ombrellaro |
| 2004/0136570 A1 | 7/2004 | Ullman et al. |
| 2004/0147840 A1 | 7/2004 | Duggirala et al. |
| 2004/0215490 A1 | 10/2004 | Duchon et al. |
| 2004/0226645 A1 | 11/2004 | Owen |
| 2004/0254466 A1 | 12/2004 | Boner et al. |
| 2005/0015011 A1 | 1/2005 | Liard et al. |
| 2005/0049498 A1 | 3/2005 | Roche et al. |
| 2005/0054923 A1 | 3/2005 | Pan |
| 2005/0054958 A1 | 3/2005 | Hoffmann |
| 2005/0102161 A1 | 5/2005 | Kalthoff et al. |
| 2005/0126291 A1 | 6/2005 | Czerw et al. |
| 2005/0150740 A1 | 7/2005 | Finkenzeller et al. |
| 2005/0154311 A1 | 7/2005 | Bruestle |
| 2005/0203396 A1 | 9/2005 | Angelsen et al. |
| 2005/0203416 A1 | 9/2005 | Angelsen et al. |
| 2005/0251035 A1 | 11/2005 | Wong et al. |
| 2005/0255239 A1 | 11/2005 | Zhu et al. |
| 2005/0265267 A1 | 12/2005 | Hwang |
| 2005/0288587 A1 | 12/2005 | Roh et al. |
| 2006/0045286 A1 | 3/2006 | Abrams et al. |
| 2006/0085049 A1 | 4/2006 | Cory et al. |
| 2006/0100529 A1 | 5/2006 | Rueckmann et al. |
| 2006/0173344 A1 | 8/2006 | Marian et al. |
| 2006/0173348 A1 | 8/2006 | Wilser et al. |
| 2006/0241423 A1 | 10/2006 | Anderson et al. |
| 2006/0241452 A1 | 10/2006 | Cerofolini |
| 2006/0241455 A1 | 10/2006 | Shvarts |
| 2006/0275171 A1 | 12/2006 | Younts |
| 2007/0011836 A1 | 1/2007 | Brewer et al. |
| 2007/0013269 A1 | 1/2007 | Huang |
| 2007/0043585 A1 | 2/2007 | Matos |
| 2007/0062290 A1 | 3/2007 | Roh et al. |
| 2007/0088213 A1 | 4/2007 | Poland |
| 2007/0096568 A1* | 5/2007 | Patt ...................... H02K 33/18 310/15 |
| 2007/0106143 A1 | 5/2007 | Flaherty |
| 2007/0156126 A1 | 7/2007 | Flaherty |
| 2007/0167813 A1 | 7/2007 | Lee et al. |
| 2007/0167821 A1 | 7/2007 | Lee et al. |
| 2007/0167823 A1 | 7/2007 | Lee et al. |
| 2007/0167824 A1 | 7/2007 | Lee et al. |
| 2007/0167825 A1 | 7/2007 | Lee et al. |
| 2007/0167826 A1 | 7/2007 | Lee et al. |
| 2007/0197954 A1 | 8/2007 | Keenan |
| 2007/0208253 A1 | 9/2007 | Slayton et al. |
| 2007/0232921 A1 | 10/2007 | Lee |
| 2007/0239075 A1 | 10/2007 | Rosenberg et al. |
| 2007/0270781 A1 | 11/2007 | Burgermeister et al. |
| 2007/0276240 A1 | 11/2007 | Rosner et al. |
| 2007/0277596 A1 | 12/2007 | Kim et al. |
| 2008/0014627 A1 | 1/2008 | Merchant et al. |
| 2008/0021317 A1 | 1/2008 | Sumanaweera |
| 2008/0027327 A1 | 1/2008 | Wilser et al. |
| 2008/0086054 A1 | 4/2008 | Slayton et al. |
| 2008/0134813 A1 | 6/2008 | Petetin |
| 2008/0136973 A1 | 6/2008 | Park |
| 2008/0167555 A1 | 7/2008 | Qian et al. |
| 2008/0269647 A1 | 10/2008 | Brunsveld Van Hulten |
| 2008/0281206 A1 | 11/2008 | Bartlett et al. |
| 2008/0287793 A1 | 11/2008 | Hoffmann |
| 2008/0287797 A1 | 11/2008 | Lee et al. |
| 2008/0287860 A1 | 11/2008 | Tgavalekos et al. |
| 2008/0300490 A1 | 12/2008 | Chiang et al. |
| 2009/0036780 A1 | 2/2009 | Abraham |
| 2009/0038315 A1 | 2/2009 | Johnson |
| 2009/0043206 A1 | 2/2009 | Towfiq et al. |
| 2009/0105597 A1 | 4/2009 | Abraham |
| 2009/0118620 A1 | 5/2009 | Tgavalekos et al. |
| 2009/0171185 A1 | 7/2009 | Chou et al. |
| 2009/0171217 A1 | 7/2009 | Kim et al. |
| 2009/0171252 A1 | 7/2009 | Bockenstedt et al. |
| 2009/0171255 A1 | 7/2009 | Rybyanets et al. |
| 2009/0177092 A1 | 7/2009 | Riechers et al. |
| 2009/0192389 A1 | 7/2009 | Eilers et al. |
| 2009/0216159 A1 | 8/2009 | Slayton et al. |
| 2009/0221917 A1 | 9/2009 | Southern |
| 2009/0247879 A1 | 10/2009 | Angelsen et al. |
| 2009/0254134 A1 | 10/2009 | Nikolov et al. |
| 2009/0281422 A1 | 11/2009 | Salama et al. |
| 2009/0299193 A1 | 12/2009 | Haftman et al. |
| 2009/0307328 A1 | 12/2009 | Nuttall et al. |
| 2009/0312638 A1 | 12/2009 | Bartlett |
| 2009/0312639 A1 | 12/2009 | Medlin et al. |
| 2009/0316854 A1 | 12/2009 | Ismail et al. |
| 2009/0318808 A1 | 12/2009 | Brader |
| 2009/0326341 A1 | 12/2009 | Furlan |
| 2010/0036240 A1 | 2/2010 | Ismail et al. |
| 2010/0036258 A1 | 2/2010 | Dietz et al. |
| 2010/0049099 A1 | 2/2010 | Thapliyal et al. |
| 2010/0056858 A1 | 3/2010 | Mokelke et al. |
| 2010/0056912 A1 | 3/2010 | Urness et al. |
| 2010/0056956 A1 | 3/2010 | Dufresne et al. |
| 2010/0063398 A1* | 3/2010 | Halmann ............... A61B 8/461 600/459 |
| 2010/0076789 A1 | 3/2010 | Pan |
| 2010/0125192 A1 | 5/2010 | Chopra et al. |
| 2010/0152590 A1 | 6/2010 | Moore et al. |
| 2010/0174185 A1 | 7/2010 | Wang et al. |
| 2010/0174189 A1 | 7/2010 | Abraham |
| 2010/0198081 A1 | 8/2010 | Hanlin et al. |
| 2010/0217125 A1* | 8/2010 | Kadokura .......... A61B 5/02007 600/443 |
| 2010/0217128 A1 | 8/2010 | Betts |
| 2010/0226555 A1 | 9/2010 | Sandstrom et al. |
| 2010/0228122 A1 | 9/2010 | Keenan et al. |
| 2010/0249602 A1 | 9/2010 | Buckley et al. |
| 2010/0256502 A1 | 10/2010 | Buckley et al. |
| 2010/0262007 A1 | 10/2010 | Medlin et al. |
| 2010/0262160 A1 | 10/2010 | Boyden et al. |
| 2010/0262239 A1 | 10/2010 | Boyden et al. |
| 2010/0274100 A1 | 10/2010 | Behar et al. |
| 2010/0280420 A1 | 11/2010 | Barthe et al. |
| 2010/0286521 A1 | 11/2010 | Betts |
| 2010/0298711 A1 | 11/2010 | Pedersen et al. |
| 2010/0305443 A1 | 12/2010 | Bartlett et al. |
| 2010/0324418 A1* | 12/2010 | El-Aklouk ........... A61B 8/4488 600/441 |
| 2010/0324423 A1 | 12/2010 | El-Aklouk et al. |
| 2011/0034209 A1 | 2/2011 | Rubinsky et al. |
| 2011/0054292 A1 | 3/2011 | Hirson et al. |
| 2011/0054296 A1 | 3/2011 | McCarthy et al. |
| 2011/0055447 A1 | 3/2011 | Costa |

(56) References Cited

U.S. PATENT DOCUMENTS

| | | |
|---|---|---|
| 2011/0080120 A1 | 4/2011 | Talstra et al. |
| 2011/0092781 A1 | 4/2011 | Gertner |
| 2011/0098571 A1 | 4/2011 | Medlin et al. |
| 2011/0098572 A1 | 4/2011 | Chen et al. |
| 2011/0105907 A1 | 5/2011 | Oakley et al. |
| 2011/0125022 A1 | 5/2011 | Lazebnik |
| 2011/0166455 A1 | 7/2011 | Cully et al. |
| 2011/0172541 A1 | 7/2011 | Anthony et al. |
| 2011/0196267 A1 | 8/2011 | Mishelevich |
| 2011/0201914 A1 | 8/2011 | Wang et al. |
| 2011/0210821 A1 | 9/2011 | Gehin |
| 2011/0237955 A1 | 9/2011 | Dietz et al. |
| 2011/0238085 A1 | 9/2011 | Berzak et al. |
| 2011/0248820 A1 | 10/2011 | Gehin |
| 2011/0270138 A1 | 11/2011 | Mishelevich |
| 2011/0270797 A1 | 11/2011 | Adams et al. |
| 2011/0301508 A1 | 12/2011 | Sethuraman et al. |
| 2011/0306886 A1 | 12/2011 | Daft et al. |
| 2011/0319760 A1 | 12/2011 | Cerofolini et al. |
| 2011/0319765 A1 | 12/2011 | Gertner et al. |
| 2011/0320143 A1 | 12/2011 | Hopkins |
| 2012/0022379 A1 | 1/2012 | Gubbini et al. |
| 2012/0022409 A1 | 1/2012 | Gertner et al. |
| 2012/0029303 A1 | 2/2012 | Shaya |
| 2012/0046548 A1 | 2/2012 | Hao et al. |
| 2012/0046553 A9 | 2/2012 | Buckley et al. |
| 2012/0053468 A1 | 3/2012 | Griffin et al. |
| 2012/0089029 A1 | 4/2012 | Harhen |
| 2012/0095347 A1 | 4/2012 | Adam et al. |
| 2012/0109018 A1 | 5/2012 | Gertner et al. |
| 2012/0172706 A1 | 7/2012 | Salminen |
| 2012/0203098 A1 | 8/2012 | Raju et al. |
| 2012/0203104 A1 | 8/2012 | Urness et al. |
| 2012/0209118 A1 | 8/2012 | Warnking |
| 2012/0245466 A1 | 9/2012 | Ganguly |
| 2012/0253239 A1 | 10/2012 | Gertner et al. |
| 2012/0271168 A1 | 10/2012 | Radojicic |
| 2012/0272738 A1 | 11/2012 | Klessel et al. |
| 2012/0289869 A1 | 11/2012 | Tyler |
| 2012/0296899 A1 | 11/2012 | Adams |
| 2013/0024704 A1 | 1/2013 | Barthe et al. |
| 2013/0066208 A1 | 3/2013 | Barthe et al. |

OTHER PUBLICATIONS

International Search Report and Written Opinion, corresponding International Application No. PCT/US2013/040381, dated Sep. 24, 2013.

Aschkenasy et al., Unsupervised image classification of medical ultrasound data by multiresolution elastic registration, Ultrasound Med. Biol., 32(7):1047-54 (2006).

Biswas et al., Venous elastography: validation of a novel high-resolution ultrasound method for measuring vein compliance using finite element analysis, Semin. Dial., 23(1):105-9 (2010).

Castellano et al., Texture analysis of medical images, Clin. Radiol., 59(12):1061-9 (2004).

Garg et al., Embolic strokes after peripherally inserted central catheter placement, Ann. Vasc. Surg., 24:1133-6 (2010).

Guo et al., A novel approach to speckle reduction in ultrasound imaging, Ultrasound Med. Biol., 35(4):628-40 (2009).

Haas, Clinical review: vascular access for fluid infusion in children, Crit. Care, 8(6):478-84 (2004).

Kim et al., Local nonlinear arterial elastic modulus reconstruction from in-vivo strain imaging and PWV, Proc. IEEE Intl. Ultrasonics Symposium, pp. 728-731 (2006).

Kim et al., Dual arterial elastic modulus reconstructions from in-vivo strain imaging and PWV, Proc. IEEE Intl. Ultrasonics Symposium, 1:377-80 (2005).

Matsushima et al., Bedside ultrasound can safely eliminate the need for chest radiographs after central venous catheter placement: CVC sono in the surgical ICU (SICU), J. Surg. Res., 163(1):155-61 (2010).

Nieuwstadt et al., Microfluidic particle sorting utilizing inertial lift force, Biomed. Microdevices, 13(1):97-105 (2011).

Oakley et al., Ultrasound-assisted peripheral vascular access in a paediatric ED, Emerg. Med. Australas., 22(2):166-70 (2010).

Park et al., Arterial elasticity imaging: comparison of finite-element analysis models with high-resolution ultrasound speckle tracking, Cardiovasc. Ultrasound, 8:22 (2010).

Patel et al., Characterization of vascular strain during in-vitro angioplasty with high-resolution ultrasound speckle tracking, Theor. Biol. Med. Model., 7:36 (2010).

Qamar et al., Evolution of acoustically vaporized microdroplets in gas embolotherapy, J. Biomech. Eng., 134(3):031010 (2012).

Reeves et al., Recent trends in central venous catheter placement: a comparison of interventional radiology with other specialties, J. Vasc. Interv. Radiol., 12(10:1211-4 (2001).

Rubin et al., Sonographic elasticity imaging of acute and chronic deep venous thrombosis in humans, J. Ultrasound Med., 25(9):1179-86 (2006).

Sette et al., First: patient safety, second: patient safety, J. Electrocardiol., 44(3):389-90 (2011).

Skippen et al., Ultrasound guidance for central vascular access in the pediatric emergency department, Pediatr. Emerg. Care, 23(3):203-7 (2007).

Stippel et al., A tissue-specific adaptive texture filter for medical ultrasound images, Ultrasound Med. Biol., 31(9):1211-23 (2005).

Tsantis et al., Development of a support vector machine-based image analysis system for assessing the thyroid nodule malignancy risk on ultrasound, Ultrasound Med. Biol., 31(11):1451-9 (2005).

Vo et al., Techniques in vascular and interventional radiology: pediatric central venous access, Tech. Vasc. Interv. Radiol., 13(4):250-7 (2010).

Weitzel et al., High-resolution ultrasound elasticity imaging to evaluate dialysis fistula stenosis, Semin. Dial., 22(1):84-9 (2009).

Weitzel, Preoperative hemodialysis fistula evaluation: angiography, ultrasonography and other studies, are they useful?, Contrib. Nephrol., 161:23-9 (2008).

Weitzel et al., High-resolution ultrasound speckle tracking may detect vascular mechanical wall changes in peripheral artery bypass vein grafts, Ann. Vasc. Surg., 23(2):201-6 (2009).

Weitzel et al., Renal advances in ultrasound elasticity imaging: measuring the compliance of arteries and kidneys in end-stage renal disease, Blood Purif., 23(1):10-7 (2005).

Weitzel et al., Feasibility of applying ultrasound strain imaging to detect renal transplant chronic allograft nephropathy, Kidney Int., 65(2):733-6 (2004).

Xie et al., Correspondence of ultrasound elasticity imaging to direct mechanical measurement in aging DVT in rats, Ultrasound Med. Biol., 31(10):1351-9 (2005).

Ye et al., Microbubble expansion in a flexible tube, J. Biomech. Eng., 128(4):554-63 (2006).

\* cited by examiner

1. ⊗ Current ↑ Field → Thrust
2. → Current ↑ Field ⊙ Thrust

Most thrust in one direction

FIGURE 5L

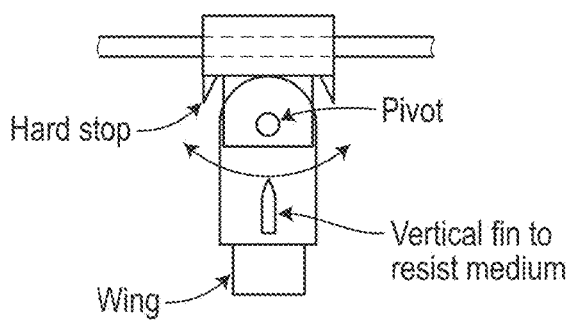

Hard stop — Pivot — Vertical fin to resist medium — Wing

FIGURE 5M

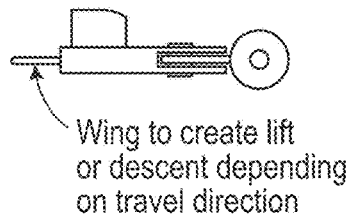

Wing to create lift or descent depending on travel direction

FIGURE 5N

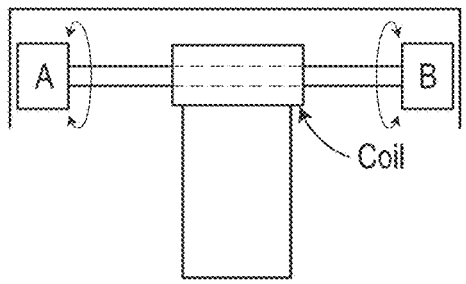

Coil

A and B are actuators (i.e. motor/solenoid) to adjust transducer angle

FIGURE 5O

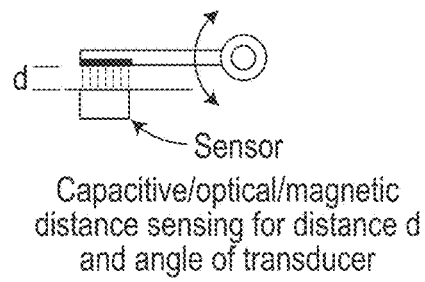

d — Sensor

Capacitive/optical/magnetic distance sensing for distance d and angle of transducer

FIGURE 5P

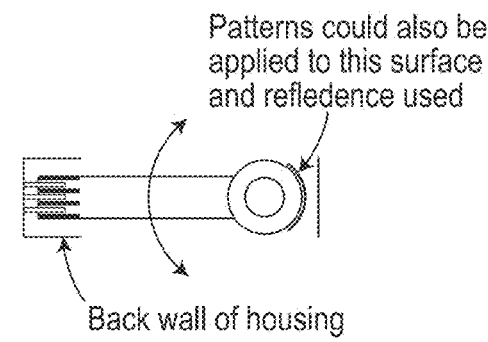

Patterns could also be applied to this surface and refledence used

Back wall of housing

Interference patterns adust brightness using 2 receivers and counting phase shifted pulses allows angle to be determined, based on transmittance

FIGURE 5Q

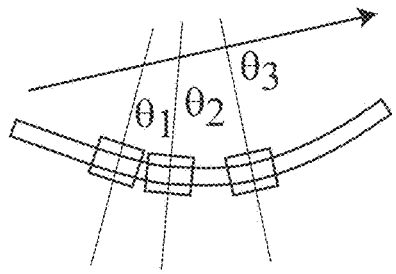

$\theta_1$ $\theta_2$ $\theta_3$

Primary motion axis can be deformed so transducer travels an arc with known trajectory

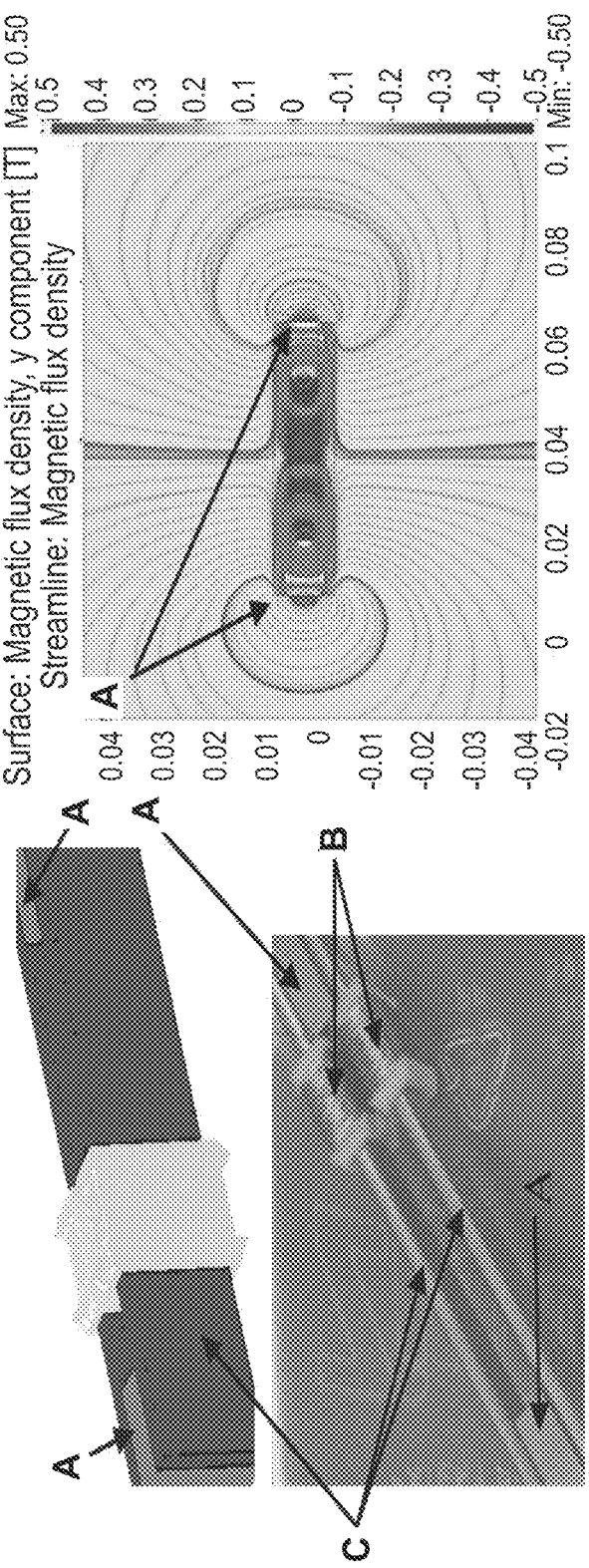

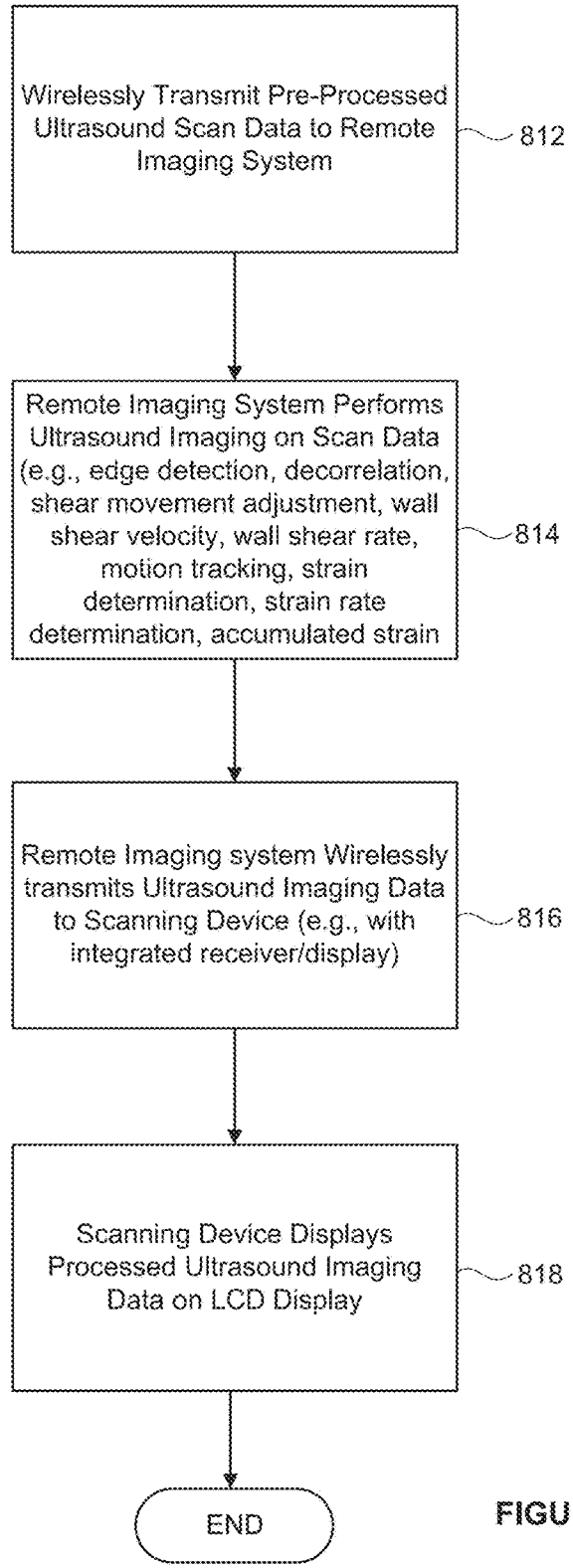

LINEAR MAGNETIC DRIVE TRANSDUCER FOR ULTRASOUND IMAGING

CROSS-REFERENCE TO RELATED APPLICATIONS

This application claims the benefit of U.S. Application Ser. No. 61/645,025, filed May 9, 2012, entitled "Linear Magnetic Drive Transducer For Ultrasound Imaging," which is hereby incorporated by reference in its entirety.

STATEMENT REGARDING FEDERALLY SPONSORED RESEARCH OR DEVELOPMENT

This invention was made with government support under HL101881 awarded by the National Institutes of Health. The government has certain rights in the invention.

FIELD OF THE INVENTION

The invention relates generally to ultrasound imaging devices and, more particularly, to linear actuator-based ultrasound devices.

BACKGROUND

Ultrasound imaging has been a core technology used in the detection and treatment of many diseases and injuries. Ultrasound imagers use high-frequency sound waves to view soft tissues such as blood vessels, muscles, and internal organs, in real-time. The transducer sends out high-frequency sound waves that reflect off of body structures, where the returning sound waves, or echoes, are displayed as an image on a monitor, where that image is formed based on the frequency and strength (amplitude) of the sound signal and the time it takes to return from the patient to the transducer. Ultrasound imagers are able to measure effects such as tissue movement or displacement and blood flow. Indeed, measuring blood vessel geometry and blood flow dynamics in vessels, such as the carotid artery, as a function of time, is considered key to cardiovascular (CV) disease identification. Another common intended application is use for procedure guidance, in particular vascular (venous, central venous, or arterial) cannulation for the introduction of device, tubes, cannulas or catheters for introducing medications or other therapeutic agents into blood vessels. Conventional ultrasound imagers use a probe with transducer array that is placed against the skin and is connected to a hand-carried (or table mounted) scanner device for signal processing.

Generally speaking, current probe-based ultrasound systems are expensive array transducer devices that employ a large array of transducer elements used to scan an ultrasound beam over an area of interest. The arrays are typically one- or two-dimensional structures formed of 64, 128, or more elements, that provide scanning over a large sample area coinciding with the size of the array. The transducers arrays are wire-coupled to an ultrasound imaging station that includes a display, input keyboard, processing machine, typically housed on a moveable frame (cart based), carry case (hand carried), or desktop machine. Recently, some have proposed what is being called a handheld (as opposed to hand carried) diagnostic ultrasound imaging device. The system is pocket-sized, incorporating a miniature display and signal processing system, connected to an ultrasound probe through a wired connection. As the probes are physically moved across the patient, ultrasound data is communicated directly to the display and processing devices for real-time imaging. The devices are small, but still cumbersome in that the operator (e.g., physician, pharmacist, or other health care provider) hold and scan the probe with one hand and hold the display/processing unit in the other hand. This can make it difficult to perform certain procedures that require the use of another hand. The result is that the ultrasound image is not always easily kept within the field of view of the operator; and, either way, the operator is limited in where they can position the display because it must be within their visual range to discern important details in the image, should ideally be within the working area of the procedure, and must be tethered to the ultrasound probe. Some have proposed modifications to such devices, such as, a tethered interface that uses a removable connection, including a docking station; but the need to control the operation of the probe still requires tethering during operation. Furthermore the devices are expensive, in large part because all image processing is performed on the portable device, which requires expensive signal processing circuitry and the associated programming.

SUMMARY OF THE INVENTION

In contrast to the conventional systems, the present application describes a low-cost, high-performance compact ultrasound imaging system able to meet the clinical point-of-care needs across various applications, such as central venous catheter (CVC) placement or assessment of stenosis of the carotid arteries based upon consensus practice criteria guidelines. The imaging system uses innovative engineering design, accurate track and hold, low-power and low-bandwidth analog to digital converters, a rectilinear or curvilinear electro-magnetic transducer drive system with motion feedback, and distributed intelligent signal processing architecture to realize a high performance ultrasound imager at low manufacturing costs.

The systems described herein employ a compact and economically-designed ultrasound transducer capable of a variety of functions, including ultrasound imaging, flow measurement, distensibility measurement, elasticity measurement, position measurement, or any number of other physical attributes of a fluid vessel, tissue, or organ. Scanned data may be used to form one-, two-dimensional (2D), three-dimensional (3D) or four-dimensional (4D) images of a sample area and in real-time.

In some examples, the scanning device includes magnetic drive assembly that scans an ultrasound transducer element along a linear path. As used herein, the term "linear path" refers to a rectilinear path, curvilinear path, or some combination of both.

In some examples, the scanning device is configured in a closed-loop control configuration. A magnetic drive controller is not only able to control scanning of the ultrasound transducer, but at the same time measure physical or electrical or optical characteristics of the magnetic drive or ultrasound transducer in a feedback manner to allow for more stable, more accurate scanning. Using a closed-loop configuration on the scanning device allows the overall system to more accurately measure certain parameters that are traditionally too difficult to measure without expensive processing equipment, parameters such as elasticity and shear adjustment.

The scanning device is part of a distributed wireless imaging system, in which a remote imaging system, such as a server or server cluster (local or distributed), is configured to receive the pre-processed scan data and perform the computationally-intensive elasticity, wall shear velocity, motion tracking (including speckle tracking for accurate motion estimation and edge detection), 3D/4D image registration, etc. operations to produce ultrasound image data that may be sent back to the scanning device for display to the operator. The scanning devices may be modular and deployed in existing ultrasound imaging processing systems. For example, the scanning devices may include wireless transceivers for communications with a remote imaging system. The modular nature is also facilitated by the front-end image processing and operator motion compensation of the magnetic drive controller. In any event, the techniques may be deployed in existing or new distributed processing configurations.

The servers may provide remote access to the processed ultrasound data via standard networking protocols, such as those supporting streaming video, audio or the display of fixed images. Commonly available devices, such as tablets, smart phones, or notebooks, etc. can be used to access and view or replay in real-time or at varying speeds the ultrasound data. This would allow the display, acquisition and processing of the ultrasound data to be spatially distributed, if required.

The server may store the raw data streams and higher-level modules will be provided to perform user-customizable analysis of the RF data, so that the image display can be adapted to provide the best rendering of the data for diagnostic use.

In some examples, additional sensors, such as accelerometers or optical scanners (e.g. such as those in an optical computer mouse) may be integrated with the magnetic drive to track the gross motion of the overall transducer assembly to provide additional information to aid 3D/4D image registration (tracking the trajectory of the device as it is moved over the surface of the skin).

In other examples, the electronic circuits to perform the generation of the acoustic wave and its subsequent acquisition may be integrated with the magnetic drive assembly to provide an integrated, compact, ultrasound scan head.

In further variations of the device, instead of a single rail guide, dual or multitude of rails or guides may be provided to guide the transducer motion along a path.

In accordance with an example, an ultrasound scanning device for providing real-time two-dimensional scan data of a sample area, the scanning device includes: a linear magnetic drive assembly defining a first scanning direction of freedom for moving an actuator of the magnetic drive assembly along a linear path; an ultrasound transducer mounted to the actuator of the linear magnetic drive assembly to scan along the linear path, in response to drive signals provided to the linear magnetic drive assembly, wherein the ultrasound transducer is to provide ultrasound scanning over a first scan plane corresponding to the sample area and extending below a surface contact area for the scanning device; and a magnetic drive assembly controller coupled to the linear magnetic drive assembly and the ultrasound transducer and applying a control for the drive signals sent to the linear magnetic drive assembly and having a sensor coupled to determine position of the ultrasound transducer during scanning of the sample area, the magnetic drive assembly controller forming a closed-loop control of the linear magnetic drive assembly and the ultrasound transducer.

In accordance with another example, an ultrasound scanning system includes: an ultrasound scanning device comprising (i) an ultrasound transducer to generate an ultrasound scan signal, (ii) a controller for controlling scanning of the ultrasound transducer, and (iii) a wireless transceiver for transmitting the ultrasound scan signal over a wireless communication network to a remote imaging processing system; and a display and receiver assembly for receiving, from the remote imaging processing system, an ultrasound image data determined from the ultrasound scan signal sent to the remote imaging processing system and for displaying the ultrasound image data on the display in real-time.

In some examples, the linear magnetic drive assembly defines a second scanning direction of freedom, different than the first scanning direction of freedom, to scan within the first scan plane.

In some examples, the ultrasound transducer defines a second scanning direction of freedom, different than the first scanning direction of freedom, to scan within the first scan plane.

In some examples, the second scanning direction of freedom is scanned electrically or mechanically.

In some examples, the linear magnetic drive assembly defines a second scanning direction of freedom, different than the first scanning direction of freedom, to scan within a second plane, different from the first scan plane for obtaining three-dimensional scan data.

In some examples, the ultrasound transducer defines a second scanning direction of freedom, different than the first scanning direction of freedom, to scan within a second plane, different from the first scan plane for obtaining three-dimensional scan data.

In some examples, the linear path is a rectilinear path.

In some examples, the linear path is a curvilinear path.

In some examples, the sensor of the magnetic drive assembly controller determines position and orientation of the ultrasound transducer.

In some examples, the magnetic drive controller includes a feedback control for ultrasound transducer head positioning.

In some examples, the feedback control comprises a sample and hold controller for compensating against operator movement of the scanning device during operation.

In some examples, the applied control is rule-based.

BRIEF DESCRIPTION OF THE DRAWINGS

FIGS. 6A and 6C are perspective views of a dual-field coil design for a magnetic actuator. FIG. 6B illustrates a magnetic circuit simulation for the configurations of FIGS. 6A and 6C.

FIGS. 11A and 11B are flow diagrams of an operation of an ultrasound imaging system, in accordance with an example.

DETAILED DESCRIPTION

Figure 1:
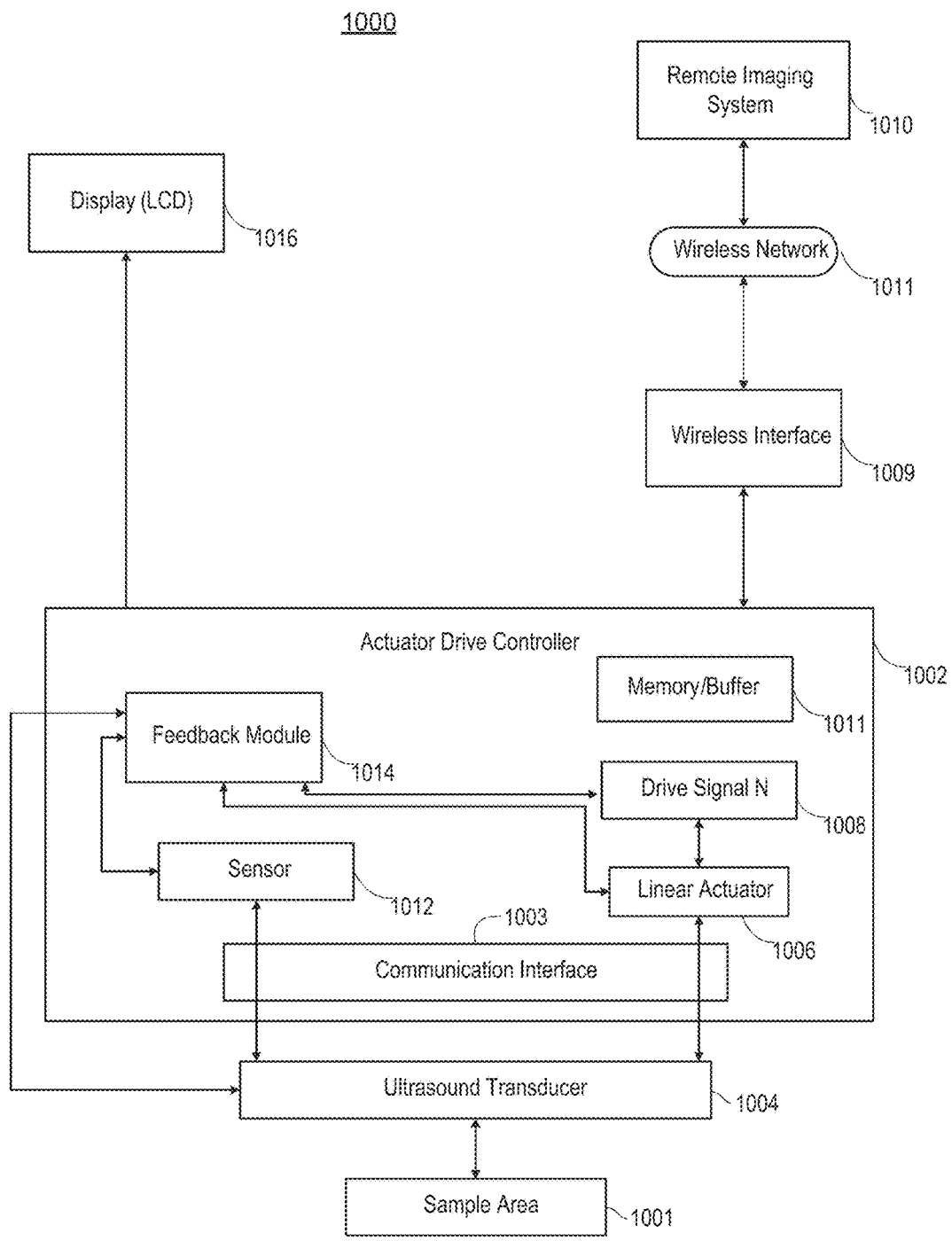
FIG. 1 is a system diagram of an example Doppler imaging system in accordance with an example.

FIG. 1 illustrates an ultrasound Doppler imaging system 1000 in accordance with an example implementation of the present techniques. Generally, the techniques provide a first device that has a single (or perhaps few) transducer elements (i) to generate an ultrasound signal and (ii) to transmit the signal data to a second device for processing the signal, a receiver to receive the processed information, and a screen display to display processed data, where the receiver and display screen may be an integrated device including the first device, or a separate device connected thereto through a wired or wireless connection. The techniques may include, for example, a simplified mechanical drive system to collect ultrasound data from a plurality of locations or orientations, and a second device for processing the data received from the first device (i.e. for distributed signal processing) and transmitting the processed data to the first device for display (or to the receiver-display unit that is separate from the first device). For example, in order to generate a 2D or 3D image, a region of interest (measurement window defining a sample area) may be evaluated by sampling wave reflections returning to an ultrasound transducer, of a handheld device, from short bursts of acoustic pulses sent periodically as the transducer traverses across the skin surface. The reflected waves may be sampled with the transducer actuation using a closed-loop control system to build an undistorted image of the underlying tissue. The sampled data may then be streamed (or streamed continuously during acquisition) to a central image-processing server (as the second device) for rendering into the ultrasound image, after which the data may be returned to the handheld device for display. The display screen may be mounted on the transducer module to allow an operator to introduce a needle into vessel during the localization procedure while remaining low profile to avoid interfering with the needle and provide the "window" to view the needle action on the vessel below the device during needle insertion.

In the example illustrated in FIG. 1, an actuator drive controller 1002 controls scanning of sample area 1001 using an ultrasound transducer 1004 through an interface 1003. The drive controller includes a linear actuator 1006, which may be implemented as a magnetically driven linear motor assembly coupled to the ultrasound transducer to provide support and positioning and to control scanning motion. A drive signal processor 1008 (coupled to or otherwise having a memory module or buffer 1005) provides control signals to the linear actuator, which is configured to move the ultrasound transducer along a linear path, e.g., a rectilinear path (i.e., a straight line), a curvilinear path, or some combination of the two. The ultrasound transducer may be a single element transducer or a limited linear array containing 2, 4, 6, 8, 16, or more elements. To provide scanning over 2D or 3D sample area, each transducer element may be further movable in angular directions off-axis from an axis defined by the linear actuator. The controller 1002 is coupled to receive RF and demodulated RF Doppler scan data from the ultrasound transducer 1004, for pre-processing of that scan data and communication thereof to a remote imaging system 1010. In the illustrated example, those communications are achieved through a wireless communication interface 1009, such as any of the IEEE 802.11a, b, g, and n wireless communication standards coupled to a wireless network 1011. In many examples herein, the linear actuator are implemented by a linear motor drive, such as a magnetic and/or electromagnetic linear motor drive.

The actuator drive controller 1002 is also able to receive sensed kinematic data from the ultrasound transducer, e.g., data indicating a physical characteristic of the transducer or linear actuator or data indicating an electrical state of one of the two (such as current, voltage, force, etc. indicating position, velocity or acceleration). The sensed data is supplied either directly from the transducer or through a sensor module 1012 to a feedback module 1014 within the controller.

That feedback module 1014 is configured to analyze the sensed data and create adjustment signals for the drive signal processor 1008. In this way, the actuator drive controller is able to control position, velocity, acceleration and other movements of the scanning ultrasound transducer. Controlling position and movement of the transducer in this way reduces nose and image misalignment that can result from patient or operator movement during scanning. As also further disclosed in examples below, a feedback module can provide operator-independent Doppler flow velocity monitoring or Doppler volume flow monitoring of vessels using VF Doppler algorithm or other scan data (or image data) registration technique.

In the illustrated example, the scanning device of FIG. 1 is implemented with a miniature, low-power wireless communication interface that allows integration of the scanning device as an ultrasound signal generation, acquisition and pre-processing device, within the transducer module, that distributes higher level signal processing to dedicated computing platforms such as the remote imaging system as shown. This allows the computing platforms to be developed separately, accelerating development and implementation of new image processing modules at lower cost than conventional architectures. The remote imaging system is able to perform the more complex image processing and transmit back to the scanning device ultrasound image data for display on an LCD 1016, or other dedicated local or remote, wireless or tethered display device.

The scanning device and imaging system 1000 of FIG. 1 may be used in any number of medical pathology screening applications. Example pathologies that may be examined include CV disease and carotid stenosis. The scanning device allows for rapid screening of high risk patients (e.g., patients with a possible stroke or TIA) and can obviate the need for more expensive follow-up testing among moderate-to-lower risk patients, for example, if the point-of-care testing is negative (e.g., asymptomatic patients with a bruit or atherosclerosis elsewhere). In addition to the degree of carotid stenosis, the present techniques may be used to determine other pathologies that have been investigated as predictors of stroke and indicators of vascular elasticity (i.e., echogenicity, surface ulceration). For example, anatomic/structural parameters such as intima-media thickness (IMT) have also been widely used as a surrogate marker of coronary artery disease (CAD). For IMT to be optimally useful, operator-induced measurement variability due to manual 2D measurements must be overcome, e.g., through the feedback module.

In some examples, a feedback module may be extended to perform various pre-image processing analyses on the scan data, such as compression and data transformations. A separate data packet module for assembling the scan data into a frame format for uplinking to a remote imaging system may also be included in the scanning device or implemented within the feedback module. In some further examples, the feedback module may perform more complex pre-imaging processing, such as automated edge detection and measurement to improve the accuracy of operator scanning data measurements. Such image pre-processing may be implemented entirely on the scanning device, partially on the scanning device and partially on the remote imaging system, or entirely on the remote imaging system. For systems desiring to reduce the amount of processing performed by the ultrasound scanning device, such ultrasound image processing would be performed at the remote imaging system. In terms of the feedback control for the magnetic linear actuator, by using a closed-loop controller, as shown, the feedback module can automatically counteract fluctuations in scan data, over scan cycles, due to operator movement. The feedback module, for example, may provide on-the-fly automatic registration of scan data, thus greatly reducing noise in the collected data. The feedback may also be based on independent local position information from the device such as an optical encoder or accelerometer in the device, or from current or voltage feedback from the electromagnetic drive itself.

The feedback module may also be configured to apply filtering algorithms to the scan data including computationally intensive image processing algorithms such as advanced filtering algorithms to improve edge crispness, adaptive texture smoothing to enhance boundary detection, and mathematically intensive computations to identify specific anatomical structures, detect lesions, or differentiate between pathological and healthy tissue. Although, in other examples, such filtering and analysis is performed partially or wholly at the remote imaging system.

Other data and image processing techniques described herein may be implemented in whole or in part on a scanning device controller, for example, in either the feedback module (like module 1014) or the drive module (like module 1008). In some examples, application specific data and image processing may be performed on the scanned data by the controller, such as determining total plaque area (TPA) and total plaque volume (TPV), which are used as accurate and robust markers of stroke prediction. By contrast, measurement variability of conventional 2D ultrasound imaging of plaque is due in part to manual registration, localization and integration of the series of 2D imaging planes. Therefore, accurate, 3D ultrasound imaging techniques as described herein can provide direct plaque visualization and TPV measurement important for the point-of-care assessment of asymptomatic patients, for serial monitoring, and for performing large-scale clinical trials.

Figure 2:
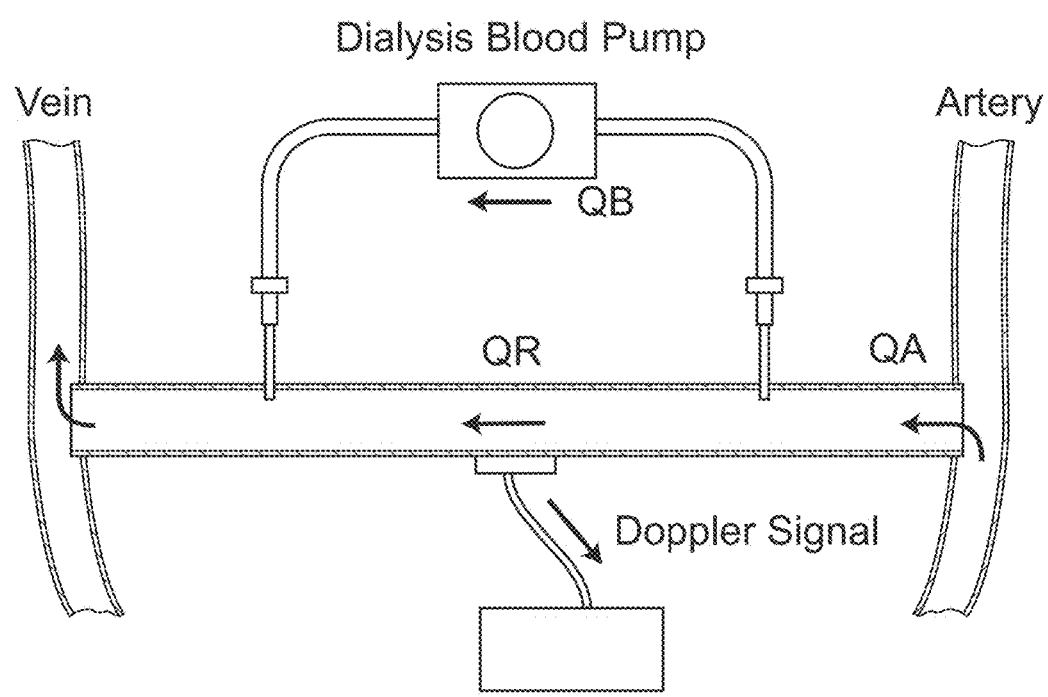
FIG. 2 is flow diagram of an example volume flow (VF) Doppler flow monitoring approach in accordance with the example of a FIG. 1.

An example implementation of the scanning device of FIG. 1, and discussed in further detail below, is as part of a volume flow (VF) Doppler analyzer. The VF Doppler technique is described in U.S. Pat. Nos. 6,167,765, 6,575,927, and 6,709,414, each of which are herein incorporated by reference, in their respective entirety. The technique allows the volume flow to be determined from low-cost Doppler velocity measurements with various pump flow rates, while at the same time reducing some of the major sources of error for typical ultrasound flow measurements. The flow velocity measurement can be acquired with a continuous-wave (CW) or pulse-wave (PW) Doppler, without disrupting treatment. FIG. 2 illustrates a flow diagram of the VF Doppler flow monitoring approach.

Figure 3B:
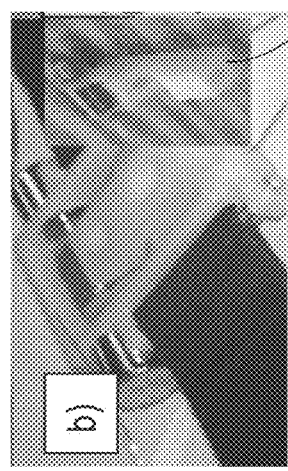
FIG. 3B is a depiction of a magnetic coil assembly as may be used in the device of FIG. 3A.
Figure 3A:
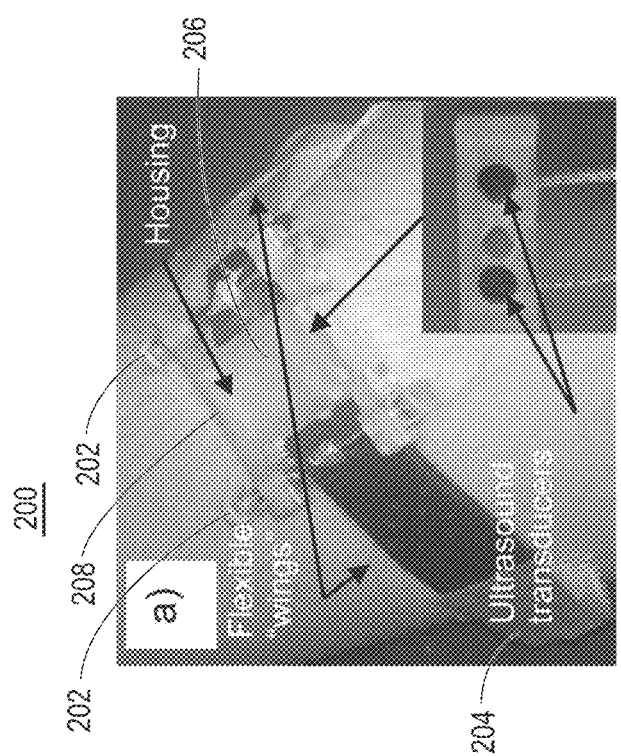
FIG. 3A is a depiction of ultrasound scanning device, with a magnetically driven linear motor, as may be used in a wrist (or limb) mountable configuration, in accordance with an example.
Figure 3C:
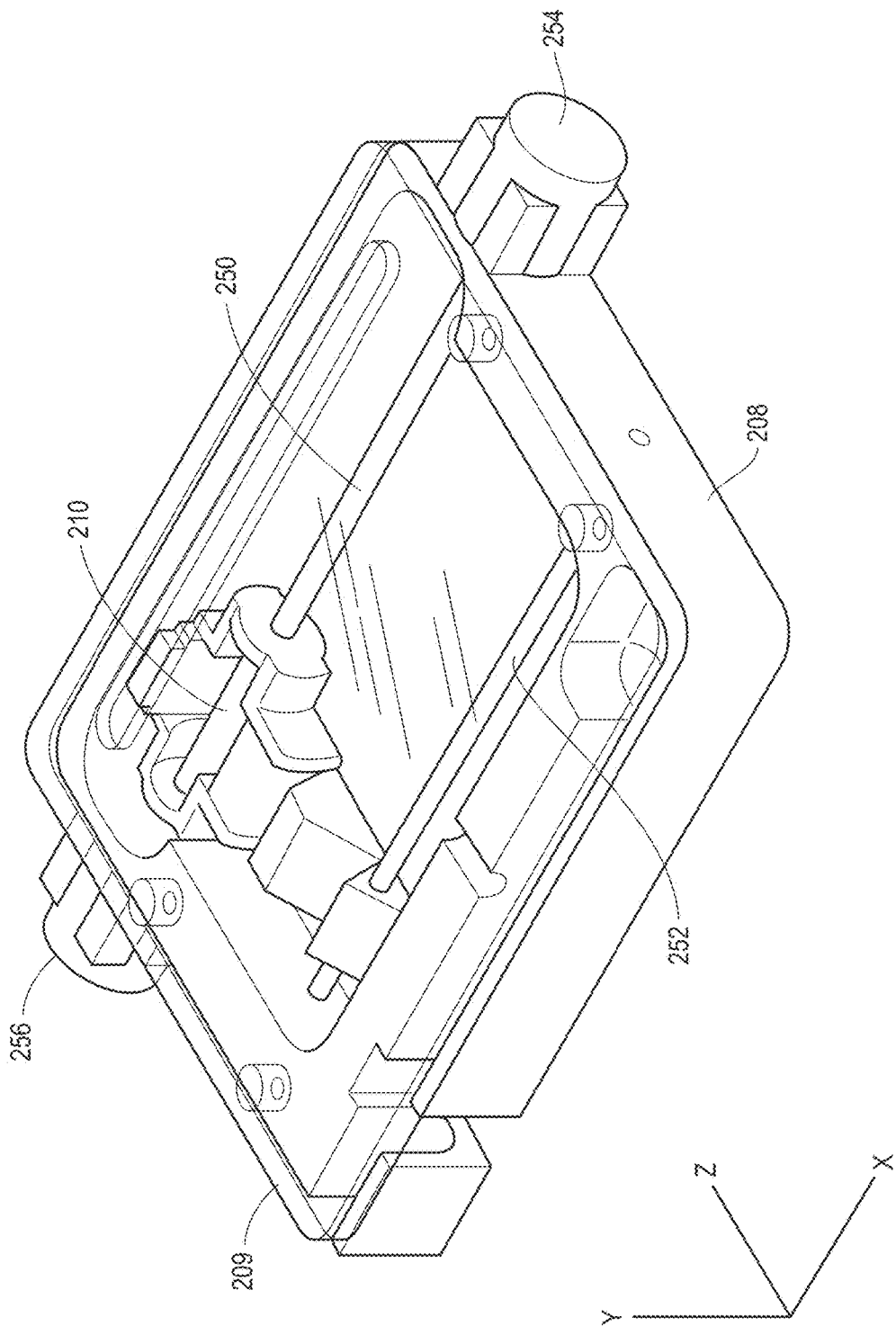
FIG. 3C is a perspective view of the device of FIG. 3A.

FIG. 3A illustrates an example implementation of the scanning device of FIG. 1, as may be used in a VF Doppler system. A band-aid type flexible transducer scanning device 200 includes mechanical fine adjustment knobs 202 attached to human arm. One or more CW Doppler transducers 204, in a single row array if multiple transducer elements are used, are positioned on a movable frame 206 located inside the housing 208 of the magnetic linear actuator 200. Or more magnetic coil assemblies are provided on the housing to move the ultrasound transducer assembly in response to received magnetic control signals. FIG. 3B illustrates an example implementation of magnetic coil assembly 210 (with winding coils not shown nor a PZT or other actuator which would be mounted to the assembly 210) of the linear actuator. The ultrasound transducer would be mounted on the coil assembly 210 with transducers adjacent a tissue surface side of the housing 208. FIG. 3C shows an example of the housing 208 in a more detailed view, showing guide rails 250 and 252 for linear movement of the coil assembly 210 and drive magnets 254 and 256. While two guide rails are shown, single, dual, or a multitude of rails could be used. The scanning device 200 would be placed over the area to be scanned and may be held in place on a permanent basis, for example, using a strap, or held in place for a small number of scans. An optical encoder may 262 (see, FIG. 3D) may be mounted to the assembly 210 and in conjunction with an encoder strip 260 (see, FIG. 3D) on the undersurface of a capping plate 209 determine position of the transducer mounted to assembly 210.

Figure 3D:
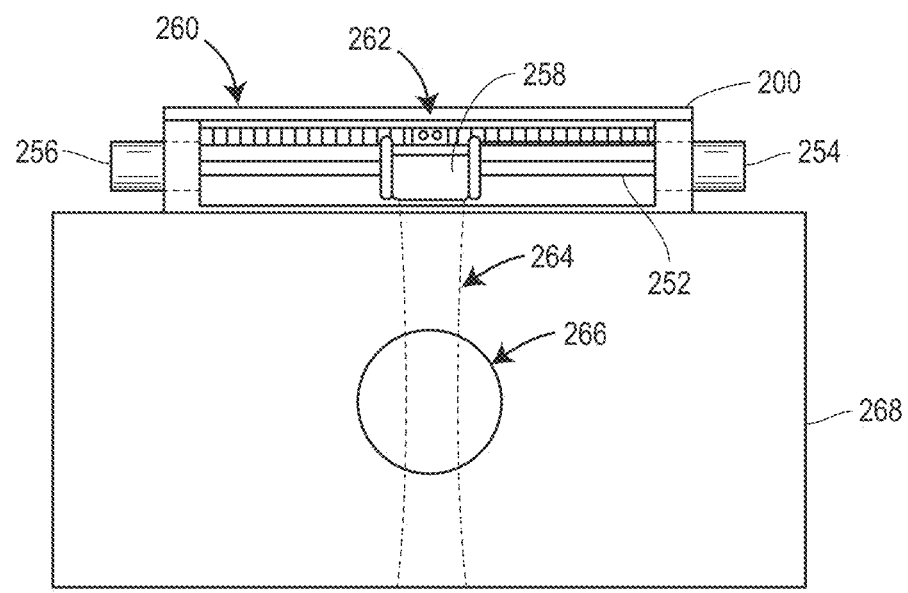
FIGS. 3D and 3E are side views of the device of FIG. 3A in first and second scan positions.
Figure 3E:
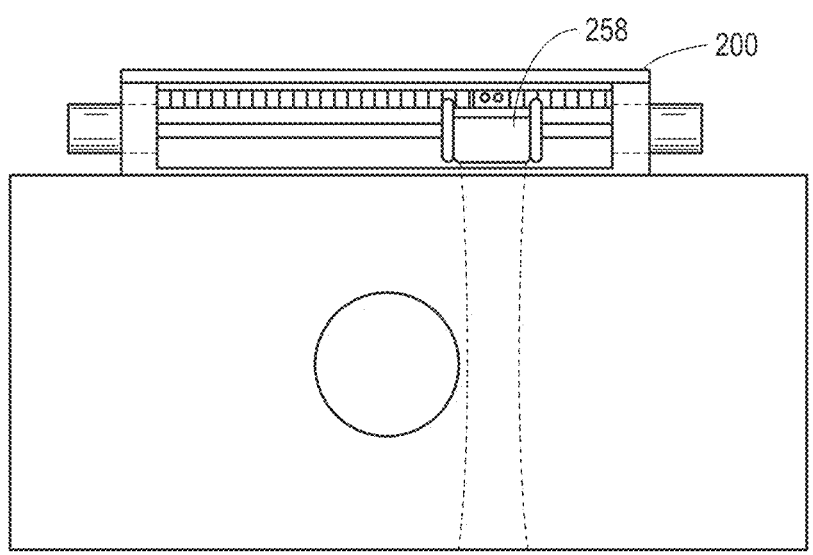

FIG. 3D illustrates a side view of operation of the scanning device 200. Transducers 204 are maintained in a transducer scan head housing 258 mounted on the coil assembly 210 (not shown) and movable in slidable direction on the rails 250 and 252 (only one of which is visible in this side view). The transducer scan head 258 includes a focusing mechanism to focus the ultrasound beam 264 into the sample region 268. The focusing mechanism may be fixed or adjustable, and mechanically adjustable or electronically. The focal point of the beam 264 coincides with a blood vessel 266, in the illustrated example. An encoder strip 260 registers a scan position of the scan head 258 via an optical encoder 262. FIG. 3E illustrates the scan head 258 is second scan position have scanned the entire blood vessel 266. Because the force provided by the linear actuator is proportional to the current flowing through the field coil and at low velocities the back EMF generated can be assumed to be negligible, and the DC resistance of the coil is constant. Therefore, the voltage applied to the field coil can be varied to control the current. Pulse wave modulation (PWM) can be used to drive the linear actuator; although a continuous differential voltage could also be used. The PWMs process includes adjusting the duty cycle of a square wave operating at a frequency higher than the mechanical system can respond. The mechanical system sees the average voltage applied, which corresponds to the duty cycle. If an H-Bridge circuit is used the direction of current through the field coils can be reversed. Using PWM with an H-Bridge provides a method for a micro-controller to digitally adjust the direction and magnitude of force delivered by a linear actuator. A spring may be included to provide a reaction force against which the linear actuator can press. Because the force exerted by a spring is proportional to its compression, and the force exerted by the field coil is linearly related to the current, one can obtain a controlled displacement or velocity by adjusting the current (duty cycle), which may also be adjusted for non-linear effects. The magnetic drive assembly controller implemented as a VF Doppler controller is shown as well and resides within a translucent plastic housing having a display for displaying Doppler data after pre-processing.

The scanning devices of FIGS. 1 and 3A-3E are able to improve the known VF Doppler technique in a number of fundamental ways.

First, operator-dependence and signal loss due to device motion is reduced. By using transducers having a fixed beam pattern, the VF Doppler device must be aligned precisely over the vascular access to avoid measurement error. If the device moves during the several-hour dialysis treatment, Doppler signal quality could be reduced or lost, requiring medical personnel to reposition the device. By using a feedback configuration with magnetic drive control, and track and hold analyses, such operator- or patient-induced error can be compensated for or eliminated entirely.

Figure 4:
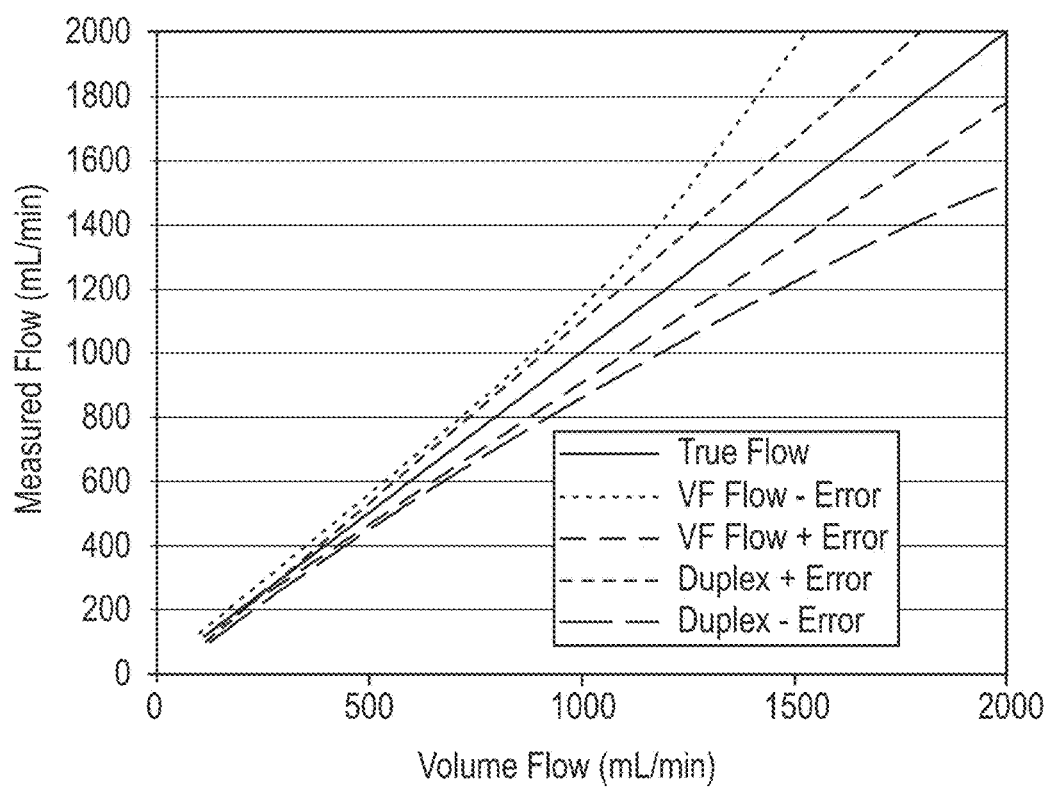
FIG. 4 is a plot of divergence of errors between a VF Doppler method and a duplex mode analysis.

Second, errors at high flow rates are reduced. The VF Doppler method is robust for flow rates <1000 mL/min, the most critical range for predicting access failure. However, in the >1000 mL/min range, which is also clinically relevant, the error inherent to the VF algorithm can rise non-linearly. To be of highest clinical value overall for access monitoring, the measurement accuracy of the device should be improved in this higher flow regime. With adaptive signal feedback and the capability to shift into "duplex mode" (i.e., vessel cross-sectional area measurement multiplied by the blood velocity to give volume flow) or a mode similar to a "duplex mode," the magnetic drive assembly is able to reduce this error. The measurement error for this mode is independent of flow rate, which means that even with an error in angle and area, accuracy may surpass the VF Doppler method as flow rates exceed 1000 mL/min. FIG. 4 illustrates an example divergence of errors between VF Doppler method alone and the duplex mode analysis.

Third, the data collected by the VF Doppler method can be used on applications beyond end stage renal disease (ESRD), of the dialysis setup of FIG. 2. Because pump-controlled flow is necessary for determining flow with VF Doppler, generally speaking, the VF Doppler method cannot be easily applied elsewhere. However, there is great demand for blood volume flow measurement for many clinical areas, including Peripheral Arterial Disease (PAD). By having motion control capabilities of the magnetic drive and feedback system produce accurate vessel size estimation and angle correction, volume flow monitoring will be possible in applications with no dialysis blood pump.

Fourth, the low-cost nature of the VF Doppler smart sensor device with the above features creates the potential to improve dialysis vascular access care, given that accurate flow monitoring will become an affordable part of every dialysis treatment. The present techniques allow the integration of the scanning device into a compact VF Doppler smart sensor for operator-independent flow monitoring. Doppler flow information acquired by the device may be wirelessly uploaded to a remote imaging system using a low-power short-range wireless link. That remote imaging system performs image processing and may be connected to or part of a medical records management system, medical alert system, or an automated drug delivery system. The remote imaging system may be integrated with decision analysis algorithms and/or risk assessment algorithms to improve diagnostic decision making. These decision support systems (DSS) may be based on demographic data or may use patient history data, and may include learning algorithms based on any number of inputs. Using these algorithms the decision support may "learn" and improve risk assessment or improve the information given to the clinical to improve diagnostic decision making. These decision support learning algorithms may be based on data collected across patient groups, historical data collected for each particular patient, or some combination thereof. Beyond the ESRD setting, there is great potential for use in Peripheral Arterial Disease (PAD), a common disease affecting 12 million people in the United States.

Figure 17:
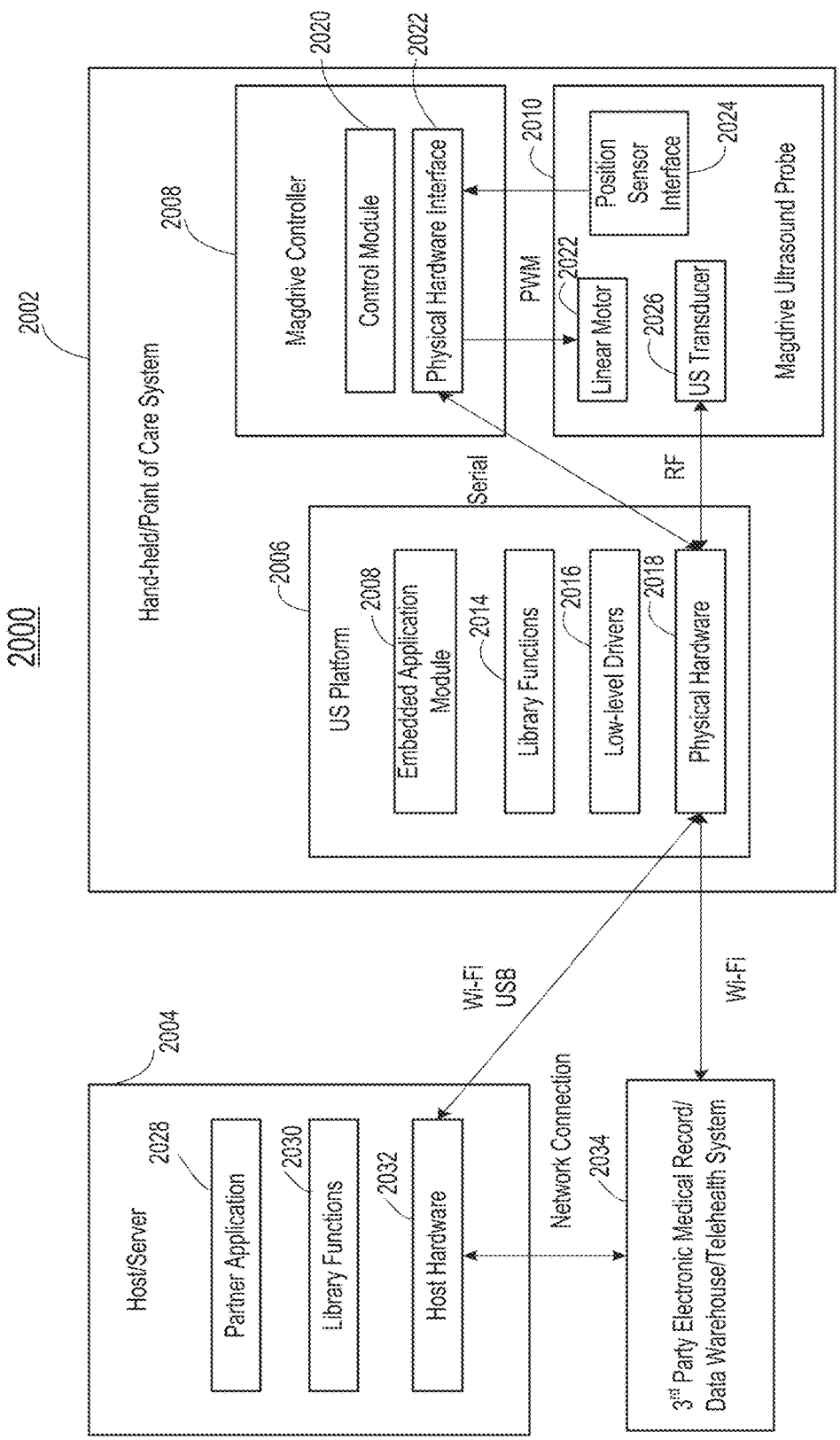
FIG. 17 is a system diagram of an ultrasound imaging system having a handheld ultrasound scanner device and a remote image processing system, in accordance with an example.

The remote imaging system may be a centralized computer system, such as a server, as shown in FIG. 17, that wirelessly communicates with numerous wireless ultrasound scanning devices (e.g., handhelds) located throughout a facility, at the patient's point of care or otherwise. The centralized computer system would communicate with the various devices through an address-specific data format that may be encrypted in some examples. The distributed approaches described herein facilitate scalability of the computational power according to the utilization (e.g., number of simultaneous scans from one device or from the many concurrently operating scanning device). Therefore, while one remote imaging system is shown, ultrasound image processing may be achieved by using numerous remote systems in a server configuration. This allows for processing of sub-sections of an image in parallel to speed up processing. Or in other examples, each of the different remote systems could have specialized processing functions, such as automated diagnosis/region of interest detection, where image data is communicated between the remote systems before sending the completed ultrasound image back to the "Doppler window" device.

FIG. 17 illustrates system 2000 having a handheld system 2002 coupled to remote system 2004, which may serve as a remote imaging system. The handheld system 2002 includes an ultrasound module 2006 a linear actuator, formed having a magnetic drive controller 2008 and a magnetically driven ultrasound probe 2010. The ultrasound module 2006 in the illustrated example includes functional blocks for performing ultrasound image processing and for interfacing with the host server 2004, for performing additional, more processing intensive image processing. An embedded application module 2012 provides high level platform providing user interface modules, display processing controls, ultrasound image storage and processing, and communications interfaces. The application module 2012 accesses library functions 2014 and low level drivers 2016 to interface with physical hardware 2018 within the handheld device 2002, controlling interfacing between that physical hardware 2018 of the ultrasound module 2006 and the actuator controller 2008, e.g., through a serial interface, and the ultrasound probe 2010, e.g., through a radio frequency (RF) interface, and through wireless (e.g., 802.11, 802.15, etc.) or wired (e.g. Universal Serial Bus) communications.

The actuator controller 2008 includes a control module 2020 that interfaces and controls a physical hardware interface 2022 in communication with the probe 2010, and more specifically, in the illustrated example, with a linear motor 2022 for the probe, a position sensor 2024, and an ultrasound transducer 2026.

The host server 2004 includes an application module 2028 for interfacing with the handheld system 2002, interfacing with a user of the server 2004, performing image processing, image data storage, etc. The application module 2028 interfaces with library functions 2030 and host hardware 2032. In the illustrated example that host hardware 2032 may include a network interface, including an ultrasound driver interface, for communicating with the handheld 2002. The host hardware 2032 may also interface with a remote data storage system 2034, such as an electronic medical records database.

Figure 18:
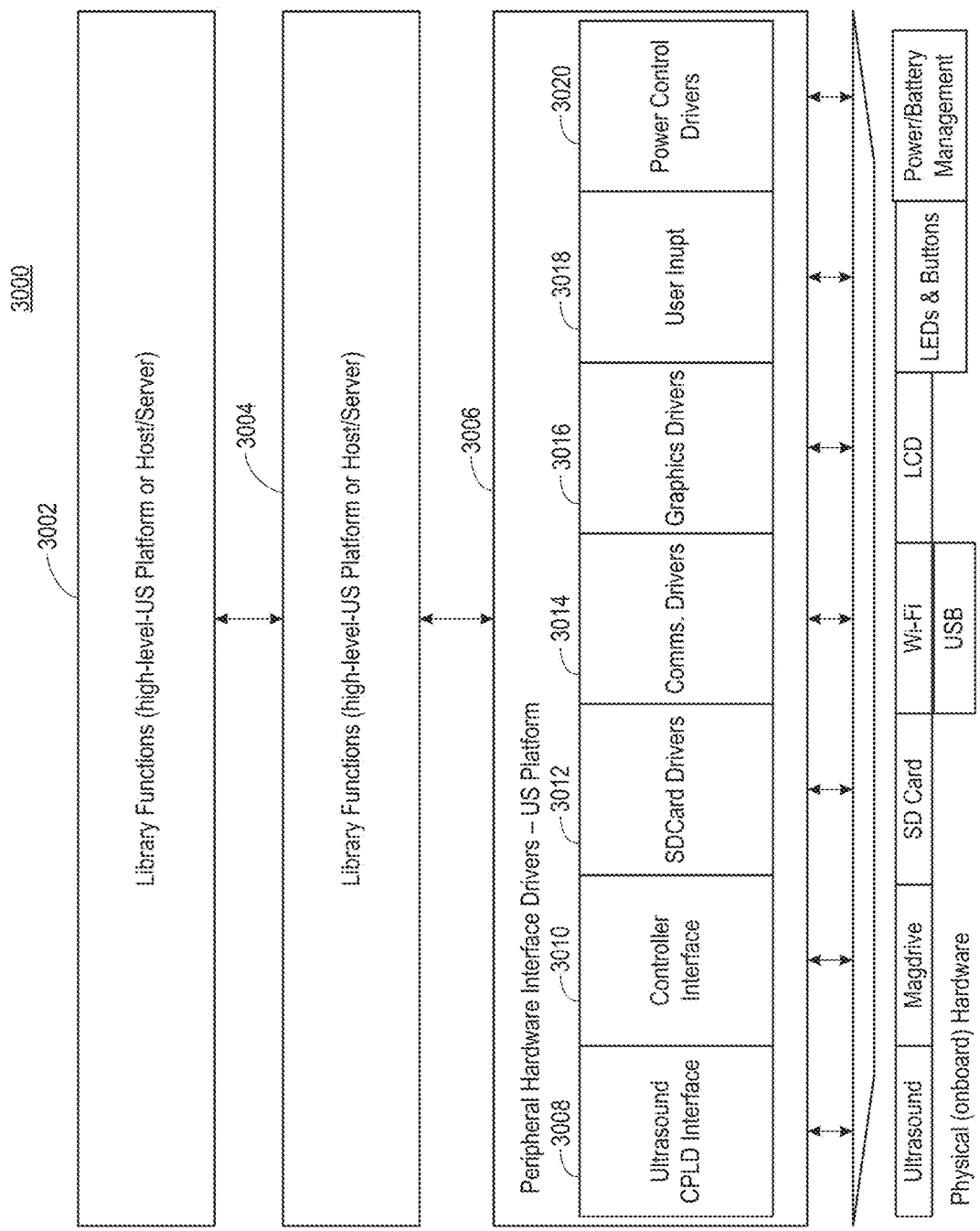
FIG. 18 is block diagram of example software modules that may be executed by the system of FIG. 17.

FIG. 18 illustrates an example implementation of FIG. 17 at a software-level where instructions are executed to perform the various operation described herein. While FIG. 18 is described as implemented in hardware, it will be appreciated that the functions described may be implemented in software, hardware, or firmware, or some combination of these. The system 3000 includes library functions 3002 that operate as high-level executable instructions at the ultrasound module and/or at the host server, such as those illustrated in FIG. 17, where these instructions include (in additional to others described herein) analyzing spectral Doppler signals, extracting flow rate from spectral Doppler signals, rendering B-mode images; compute correlation coefficients, computing speckle motion, detection motion in a scan field, computing motion region dimensions and area, connecting to databases (SQL, MySQL, Oracle, etc.), and uploading analyses to the database. Low-level library functions 3004, as may be implemented specifically by the ultrasound module in the handheld, are also shown. The instructions include instructions such as configuration instructions for the ultrasound module, establishing remote hosting, establishing file on a local storage, opening buffer memory in RAM, acquiring n 1-D beams, acquiring n 2-D images, configuring the magnetic linear actuator, and synchronizing the linear actuator with the ultrasound transducer.

The peripheral hardware interface drivers for the ultrasound module, e.g., the physical hardware interface 2018. An ultrasound CPLD interface 3008 is able to send n pulses using the ultrasound transducer, gate the receiver control for the received ultrasound signals, and set the pulse repetition frequency. A controller interface 3010 provides positional control for the linear actuator, such as instructions to move home, move at a velocity x to scan a sample area, etc. Local storage driver 3012 is shown in an example SD Card driver and interface. A communications driver 3014 is able to connect to an access point and send and receive raw data from/to the handheld for processing. A graphics driver 3016 is also shown, for displaying any instruction menus on a LCD for user input, and to display depictions of the collected image data. A user input is also shown 3018, along with power control drivers 3020 for the handheld, which include instructions to shutdown the linear actuator, shut down the handheld device, or at least put the device in a sleep mode for battery status storage.

Figure 5A:
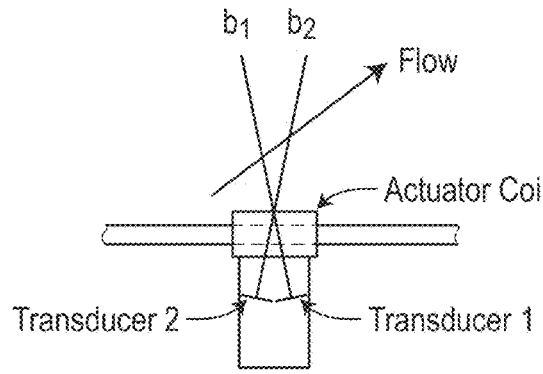
FIGS. 5A-5Q illustrate various aspects of example magnetic drive assemblies as may be used in scanning devices, in accordance with various examples.

FIGS. 5A-5Q illustrate various aspects of example magnetic drive assemblies as may be used in the scanning devices described herein. While, a single rail guide linear actuator is illustrated, dual or multitude of rails or guides may be provided to guide the transducer motion along a path. Some rails or guides may be used to generate the primary actuation force, while other may be used to constrain the motion. Either the rails themselves may be electrically or mechanically manipulated or deformed, or axes not constrained by the rails may be subjected to forces to induce variations to the transducer path. For example, if a single rail with circular cross-section is used, the transducer may be free to rotate around the rail. A magnetic field may be applied in such a fashion to induce a torque to the transducer. Feedback of the angular position could be used to magnetically levitate this axis at a controlled elevation to control scanning. This could be used to control the angle of isonification for Doppler based flow measurements, or could be used to sweep the transducer in an arc, so together with the linear motion, a 3D volume could be scanned. These techniques of actuation for these additional axes could be, but do not need to be magnetic. Methods employing piezoelectric motion or motion occurring due to interaction with the other mechanical components including fluids incorporated within the device could be used.

In any event, any suitable mechanisms for obtaining additional angle change in conjunction with using magnetic drive mechanism may be used. Some examples include those illustrated. For example, the angle information may be related to the trajectory of blood flow, where knowing the trajectory of the flow, automatic angle correction of both the azimuth and elevation of the blood flow may be achieved. The angle of the flow can be determined when two discrete angles are used for the isonification beam. This allows the resolution of both the azimuth and inclination of a flow field relative to the polar coordinate system associated with the ultrasound transducer. Resolving both these angles allows accurate direct measurement of the blood flow velocity through a vessel using simple, low cost Doppler ultrasound technology. Utilizing, pulsed-wave (PW) ultrasound with the linear transducer and resolving the accurate blood flow velocities over a 2D plane, allows the direct measurement of the blood volume flow though a vessel per unit time to be determined. This may be used along with a clinically-significant metric for peripheral artery assessment.

Because the common expression for Doppler shift would assume the acoustic wave from the transducer propagates parallel to the blood flow, the expression becomes insufficient in some peripheral vascular applications, where it is difficult to align the ultrasound transducer on the surface of the patient's skin to meet the this parallel flow constraint. The vessel most likely runs approximately parallel to the surface of the skin, but do not run perfectly perpendicular to the surface of the skin. Since, no Doppler shift is detected if the transducer is perpendicular to the vessel, an ultrasonographer may apply some angle between the transducer (and acoustic wave), and the vessel under investigation, termed the Doppler angle, θ. Typically, this is estimated from an ultrasound B-mode image and manually entered as a correction factor into the ultrasound machine. Equation 3 provides the typically used equation to determine the expected Doppler frequency shift when the Doppler angle is known. FIGS. 5A-5S illustrate various aspects of using angle deflection during ultrasound scanning and/or ways to correlate Doppler angle to vessel position and blood flow direction. The angle deflection is able to create scanning in a second direction at an angle to that of first scanning direction defined by the axis of the guide rails.

Figure 5B:
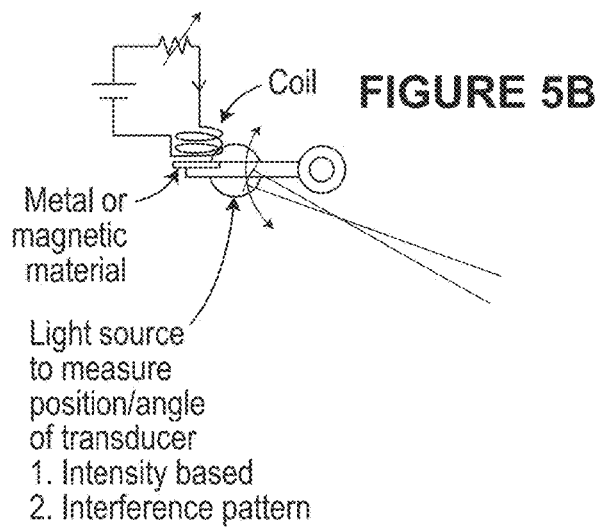
Figure 5C:
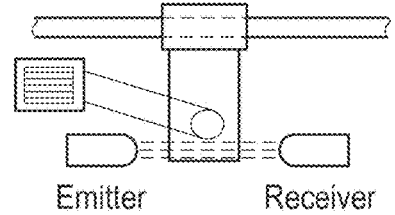

Because the transducer may be moving in a liquid medium to facilitate acoustic coupling, fins or other measures of resistance can be integrated into the transducer design, to create a torque, rotating the transducer around a pivot when translating to the left (i.e. to the left, to downward), and rotating in the opposite direction when translating to the right. See, e.g., FIG. 5G.

Magnetic levitation for precise angular control may utilize an angular sensor and actuator. See, e.g., FIG. 5B.

Figure 5D:
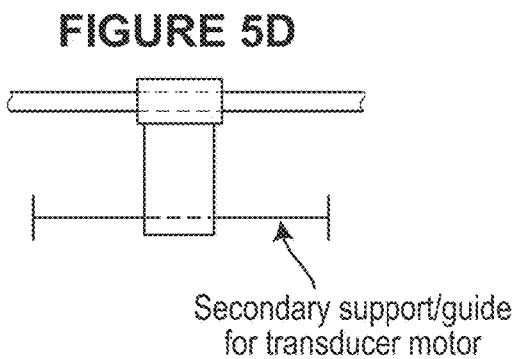

Discrete mechanical actuator (i.e. solenoid) to adjust angle is shown in FIG. 5D.

Rotation of the scan head guide, using stepper or servo-motor is shown in FIG. 5C.

Figure 5E:
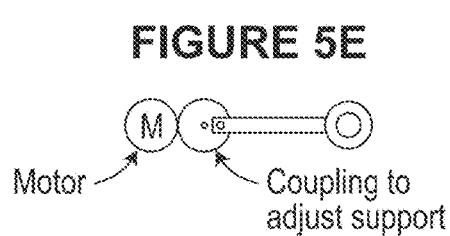

An additional winding on the primary actuator to induce a torque on the transducer head is shown in FIG. 5E.

Figure 5F:
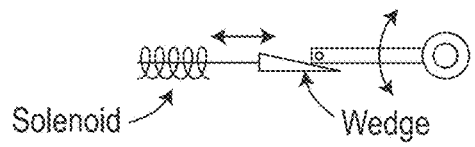
Figure 5G:
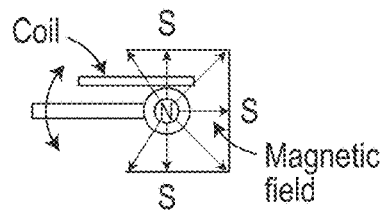

Implement dual windings on the primary actuator coil 90° (or as appropriate) relative to each other, each at 45° (or as appropriate) to the primary thrust direction. Should a balanced actuation current be applied to both coils, thrust parallel to the primary direction of motion will result. If there is an imbalance in the current supplied to each winding, a torque will be developed, allowing rotation around the primary motion axis. See, e.g., FIG. 5F.

Figure 5H:
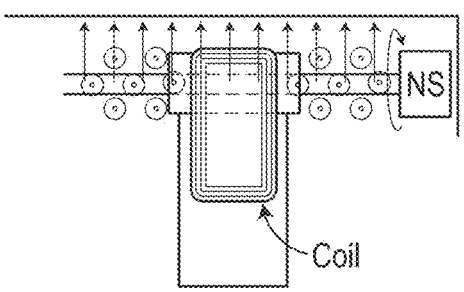

Adjustment of the primary motion axis to rotate transducer is shown in FIG. 5H.

Utilized deformation of the primary motion axis to control trajectory along an arc is shown in FIG. 5L.

Figure 5I:
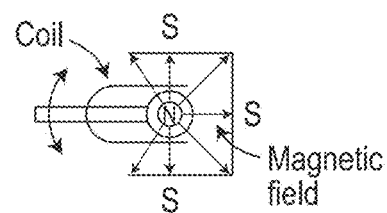
Figure 5J:
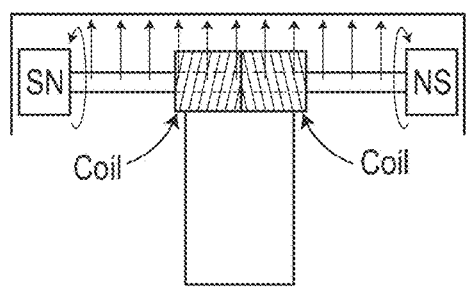
Figure 5K:
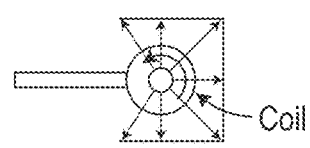

Integrating two statically offset transducers in the ultrasound scan head with known angle difference between them is shown in FIG. 5A Capacitive, inductive, or optical distance measurement between transducer and transducer housing (see, e.g. FIGS. 5I and 5K) applies to angle actuation concepts of FIGS. 5B, 5C, 5D, 5E, 5F, and 5H.

Optical interference patterns (see, e.g., FIG. 5J) applies to angle actuation concepts in FIGS. 5B, 5C, 5D, 5E, and 5F.

Linear optical encoders, or accelerometers can be used to measure position along a rail of known geometry as is shown in FIG. 5L.

In other examples, a linear 1D or 2D ultrasound array may be used instead of a single transducer element and both mechanical and electrical beam forming used to acquire the ultrasound data. The ability to adjust the transducer angle as a function of position or time provides the opportunity to implement synthetic aperture techniques in order to improve the resolution of the resulting ultrasound image.

The magnetic drive is a linear actuator in the present examples, although any number of alternative actuators may be used. A wire-element carries a current and responds to magnetic fields for actuation. The force on a wire-element of length carrying a current of magnitude in a static magnetic flux density is given by fundamental equations including Maxwell's Ampere Law, Faraday's Law, and the electric Form of Gauss' Law and Magnetic Form of Gauss' Law provided in the following well known forms:

$$F = i\vec{dl} \times \vec{B}, \nabla \times \vec{H} = \vec{J} + \frac{\partial \vec{B}}{\partial t},$$

$\nabla \cdot \vec{D} = \rho$, $\nabla \cdot \vec{B} = 0$, where, $\vec{E}$ is electric field intensity, $\vec{D}$ is electric flux density, $\vec{H}$ is magnetic field intensity, $\vec{B}$ is magnetic flux density, $\vec{J}$ is current density, $\rho$ is electric charge density. We maximize force F by design of the magnetic circuit in conjunction with armature design to ensure frictional losses are overcome. FIGS. 6A and 6C illustrate a dual-field coil design with a travel of about 2" developed for the actuator. The magnetic circuit selected after analysis contained two Neodymium Iron Boron (NdFeB) magnets with a rectangular cross-sectional thickness of 0.21" (red) attracting two steel bars (blue) $\frac{1}{8}^{th}$" thick forming the armature and motion slide/guide, as shown in FIG. 6C. The coils of the armature are wound onto 2 plastic formers; the actuators that support the ultrasound transducer. In FIG. 6B, note that comparatively strong magnetic flux density resides within the confines of the steel bars and falls rapidly external to this region. This is desirable to reduce the effects of high magnetic fields outside the device. Importantly, the direction of the magnetic flux density is nearly orthogonal to the armature coil direction maximizing the force generated, $\vec{idl} \times \vec{B}$. FIG. 6A illustrates a CAD model of components; FIG. 6B illustrates a COMSOL magnetic circuit simulation; and FIG. 6C illustrates a prototype immersed in mineral oil (ultrasound coupling medium) used for evaluating design.

Figure 7A:
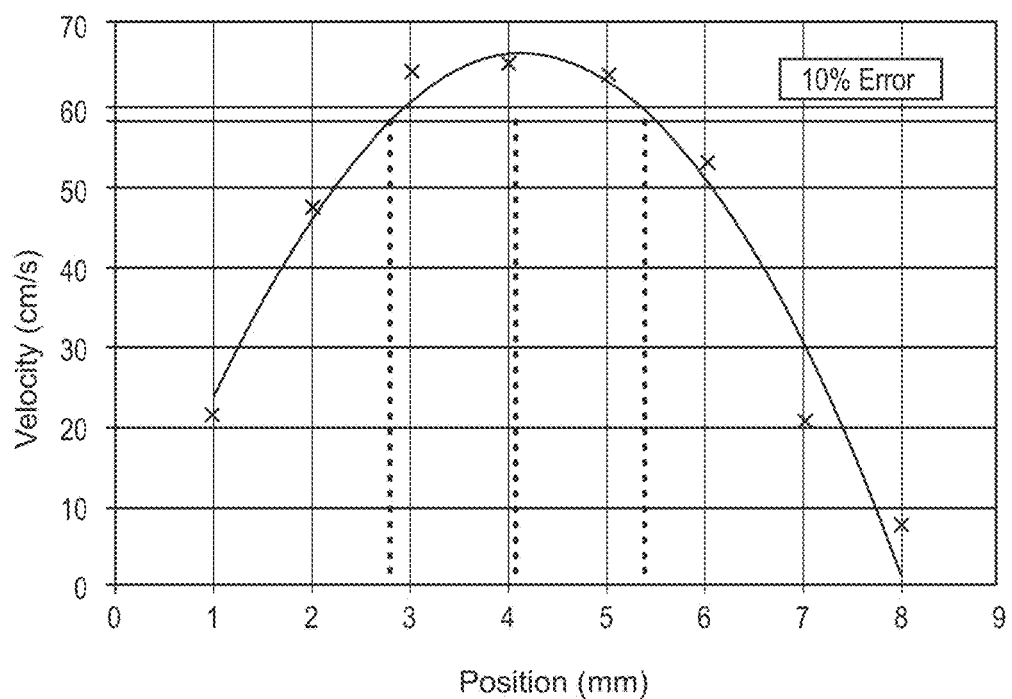
FIG. 7A is a plot of position versus velocity for an example movement of a linear motor.

FIG. 7A shows a typical flow profile obtained during a laboratory experiment on the flow phantom. The x-axis represents the flow measurements. A $2^{nd}$ order regression function has been fitted to the data to illustrate the flow profile as the ultrasound transducer is manually moved across the access. Typically, in clinical settings, this motion would be classified as a measurement error due to patient movement, positioning error or other factors. It can be seen that the maximum flow rate measured in this experiment was about 65 cm/s. If less than 10% measurement error is required due to transducer misalignment or patient motion artifacts, a positioning error of less than 1 mm is required and our design will meet 0.1 mm position control or better. The scanning device may be programmed to track across the access, scan and record so the linear actuator can return to the optimal location. Using the same scanning technique, estimates can be made about the vessel diameter.

Figure 7B:
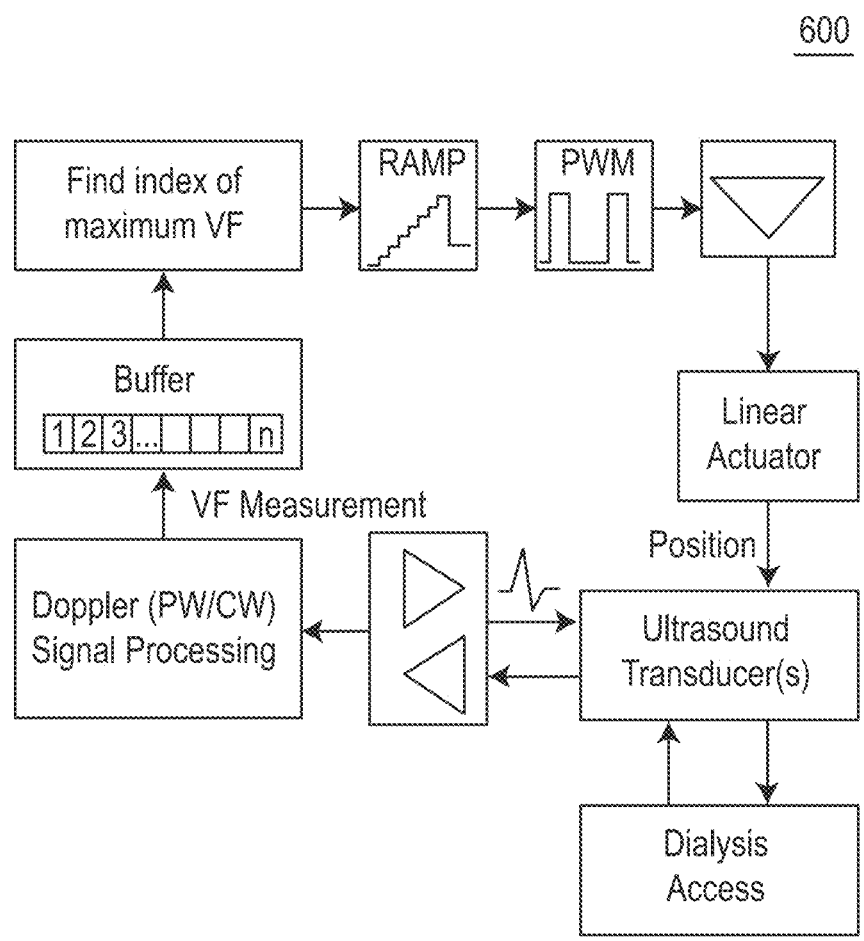
FIG. 7B is a block diagram of a control system of scanning device to compensate for transducer motion in a dialysis configuration.

FIG. 7B illustrates an example control system 600 that may be implemented on the scanning device to compensate for transducer motion to enable blood volume flow measurements to be obtained in a dialysis configuration. Because the force provided by the linear actuator is proportional to the current flowing through the field coil and at low velocities the back EMF generated can be assumed to be negligible, and the DC resistance of the coil is constant, the voltage applied to the field coil can be varied to control the current. One way to achieve this is by using PWM, which includes adjusting the duty cycle of a square wave operating at a frequency higher than the mechanical system can respond. In this way, the operation may be similar to that described in reference to FIG. 3B.

Should stick-slip become an issue; the controller may be configured to vibrate the actuator at periodic times or in response to a sensed physical condition or electrical condition, to keep the system in the kinetic friction region. An alternate solution to static friction would be to implement a pull-out boost current phase when the linear actuator begins moving. Either of these methods may be used in a singular open-loop configuration. While in other examples, the closed-loop position control formed by the feedback module may be used, such as by using back-EMF velocity measurement (integrated to get position) or optical position measurement. For the back-EMF method, the voltage generated by the field coil during the off-phase of each PWM cycle may be measured by the feedback module are sent to the feedback module, where the magnitude is proportional to the velocity of the coil. The optical position measurement approach may use a series of high-resolution (0.1 mm) transmissive or reflective marking inside the housing, which can be counted as the field coil moves along the armature.

Figure 8:
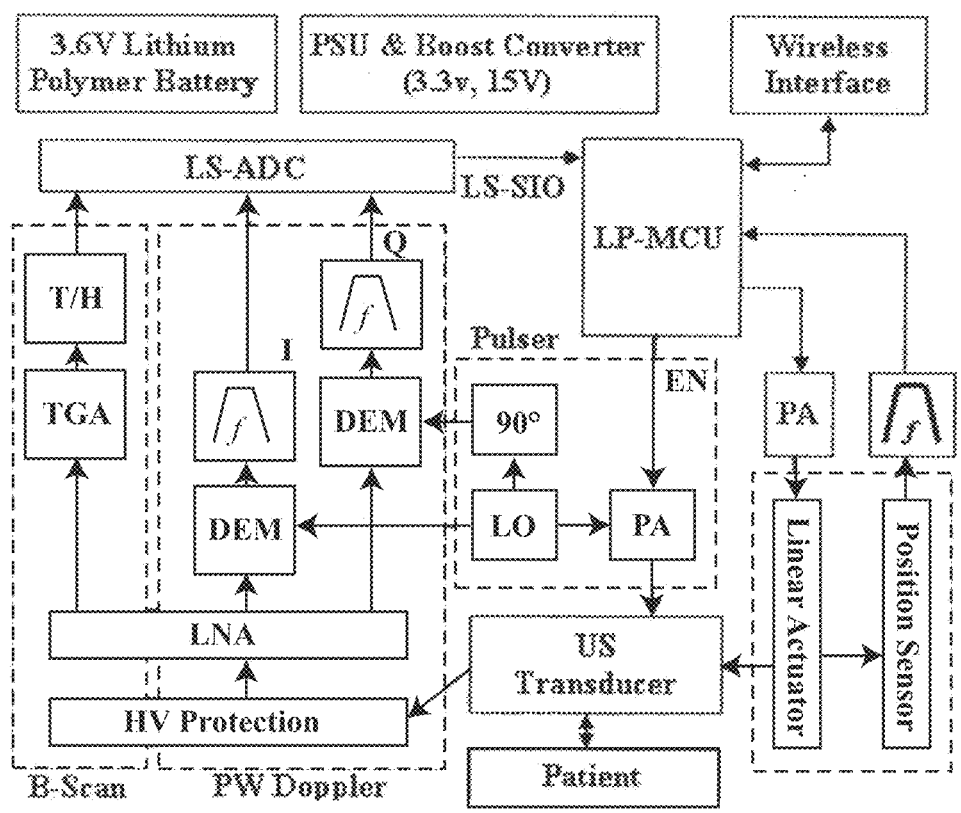
FIG. 8 is a block diagram of a scanning device in accordance with another example.

FIG. 8 illustrates a scanning device 700 in accordance with another example implementation. The scanning device may be powered by a 3.6V Lithium Polymer rechargeable battery. A low-power microcontroller (LP-MCU) controls the ultrasound transducer (single element or few elements in a one dimensional array) pulsing and acoustic signal acquisition by a low-power analog to digital converter (LP-ADC) over a simple low-speed serial interface (LS-SIO) running at 32 MHz. Along with the power supply (PSU) and boost converter, the power amplifier (PA) provides the current and impedance matching circuitry for correct pulsing. A transducer frequency of between 5-10 MHz has been chosen to allow appropriate imaging depth, since the acoustic wave attenuates at around 0.5 dB/MHz/cm for soft tissue. The high-voltage (HV) protection, transmit-receive switch prevents saturating or damaging the time-gain low-noise amplifier (LNA). The receive signal conditioning circuitry is divided into a special block preparing the RF signal for direct sampling for B-scan imaging, and a parallel block for bi-directional PW Doppler using hardware based baseband I/Q demodulation.

For implementations such as PW Doppler constructing 2D images of the bi-directional blood flow, the sampling rate will be substantially below the high-speeds of standard ultrasound machines. This means that Baseband Quadrature Demodulation may be performed in the analog domain with the local oscillator tuned to the transmit frequency. After digitization, the signal is processed through a standard Fast Fourier Transform (FFT).

The scanning device may be designed with any standard depth of interest, were 4 cm is a preferred depth that may be achieved using the acoustic wave in tissue of 1500 m/s, allowing the pulse duration in the tissue to be around 53 micro-seconds. The acoustic wave velocity in tissue limits the pulse-to-pulse sampling rate of the system to around 18 kHz. At 2 MSPS, each pulse will be sampled 106 times, once every 500 ns (1.5 mm resolution). For a three-fold increase in resolution (0.5 mm), two additional ADCs can be used with staggered sample delay. If a 64-point FFT is generated, 64 pulses at the same location are taken, requiring a total of about 3.4 ms to complete. For a 3 cm wide area to be investigated at a resolution of 0.5 mm, 60 lateral scan-lines yield 0.2 s per image, resulting in a 5 Hz frame.

Figure 9:
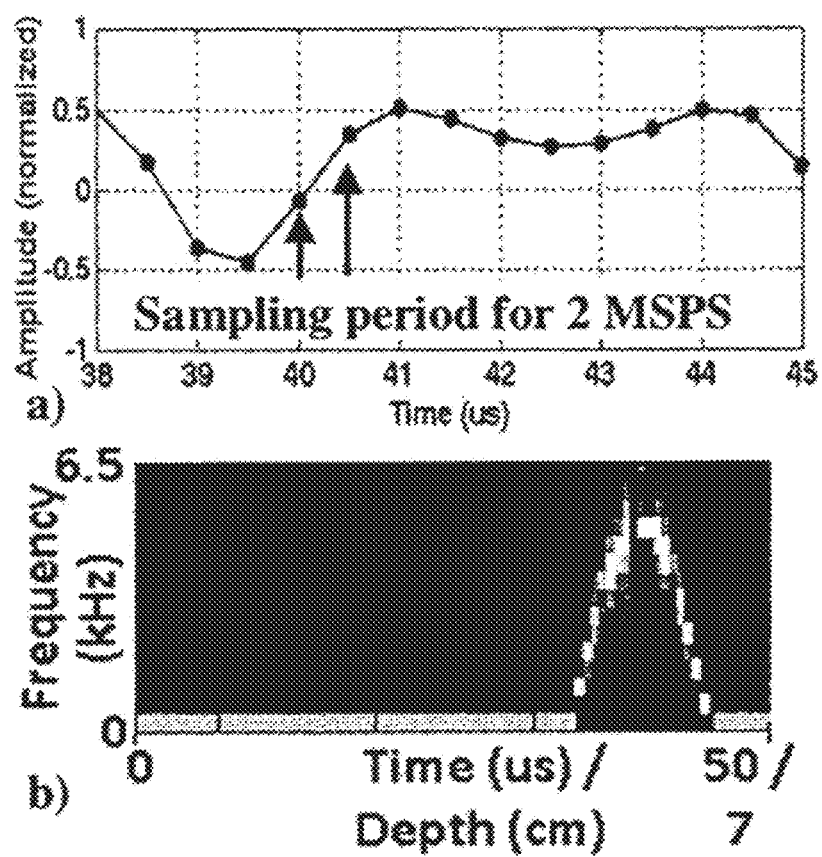
FIG. 9A is a plot of sample period versus amplitude for a scan using a single pulse drive, in accordance with an example.
FIG. 9B is a spectrogram plot that results from the operation in FIG. 9A.

FIGS. 9A and 9B illustrate the results of a MATLAB simulation constructed to test the sampling method for obtaining the flow information for a single scan line. A parabolic flow profile 1.5 cm wide with a peak frequency shift of 5 kHz was constructed approximately 3 cm below the surface. Depth dependent attenuation was considered to be compensated for by the time gain amplifier. FIG. 9A provides a snapshot of the sampling over 7 micro-seconds for a single pulse using a 2 MSPS ADC (0.5 us sampling period). Over the sampling period the acoustic wave will propagate 0.08 mm. This pulse-sample procedure is repeated 64 times at a rate of 25 kHz in order to gather sufficient information to generate an FFT at each discrete depth as well as obey the Nyquist criterion. FIG. 9B provides the resulting spectrogram, where each vertical slice comprises a single 64-point FFT.

The scanning device in FIG. 8 is a dual mode device, having a PW Doppler scanning stage and a B Scan scanning stage. The B-scan imaging may be performed in parallel with the PW Doppler imaging operating at 8 MHz. Sampling at greater than twice this frequency is required according to the Nyquist criterion. Practically, however, approximately 10 data points per wave period are used, resulting in standard sampling of the reflected waves at around 80 MSPS. This customarily requires a high-speed ADC, special digital interfaces, and a sufficiently powerful processor with adequate storage to handle the data bandwidth and associated signal processing. All these architectural factors significantly increase the complexity, power budget, size and cost of these systems. The present techniques, by contrast, use a lower speed (2 MSPS) ADC and a high performance track and hold front-end. Sequential acoustic pulses will be transmitted, shifting the point at which sampling begins in order to fulfill Nyquist sampling criterion. Table 1 shows example frame rates that may be achieved.

TABLE 1

Estimated frame rate trade-off between lateral and axial resolution, and scan depth.

| Lateral resolution | Axial resolution | Scan Depth (cm) | | | |
|---|---|---|---|---|---|
| (mm) | (mm) | 2.00 | 4.00 | 6.00 | 8.00 |
| 0.25 | 0.5 | 10 Hz | 5 Hz | 3 Hz | 3 Hz |
| 0.5 | 0.5 | 21 Hz | 10 Hz | 7 Hz | 5 Hz |
| 0.75 | 0.5 | 31 Hz | 16 Hz | 10 Hz | 8 Hz |
| 0.25 | 1 | 21 Hz | 10 Hz | 7 Hz | 5 Hz |
| 0.5 | 1 | 42 Hz | 21 Hz | 14 Hz | 10 Hz |
| 0.75 | 1 | 63 Hz | 31 Hz | 21 Hz | 16 Hz |
| 0.25 | 1.5 | 31 Hz | 16 Hz | 10 Hz | 8 Hz |

Figure 10:
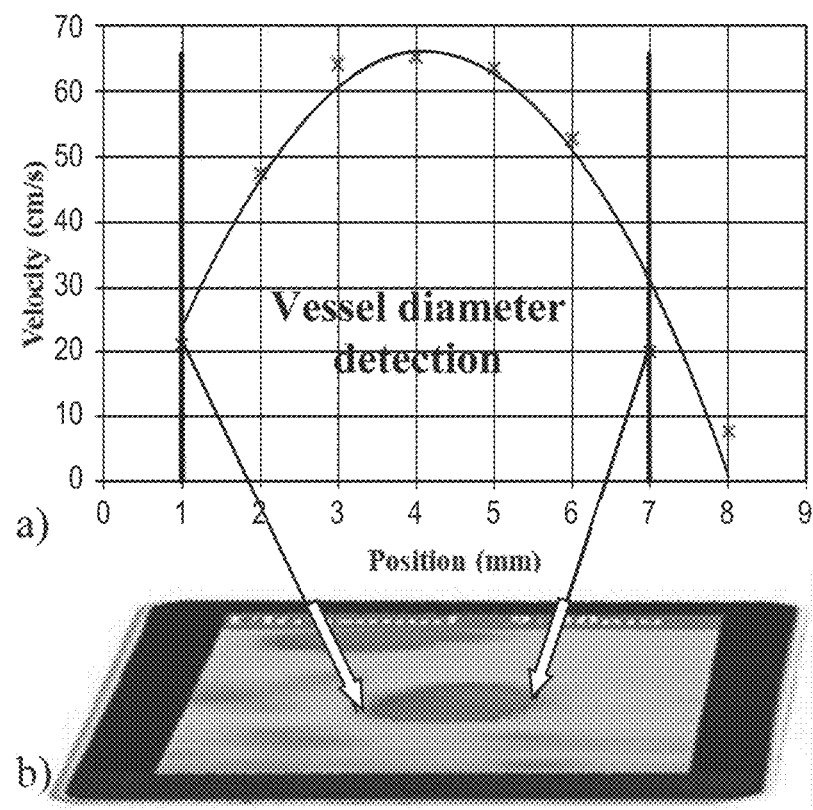
FIG. 10A is a plot of scan position versus velocity.
FIG. 10B is an image of the corresponding pulse width Doppler image (or B mode image data), in accordance with an example.

Used in a "Doppler Window" application, in which the scanning device communicates the scan data to a remote imaging system for formation of the ultrasound image, the acquired data from the scanning device will be streamed over a wireless link (scan-line and/or 8-bit decimated Doppler I/Q channels=2 MSPS×2 bytes=32 Mbps uncompressed with no headers) to a signal processing server, e.g., the remote imaging system, where the FFT and associated processing may be performed and where the rendered image is returned back to the display on the hand scanning device for display, minimizing the complexity of the imaging hardware. FIGS. 10A and 10B provide an example of image processing that will be performed, in order to display the vessel for cannulation. The data in FIG. 10A, similar to that of FIG. 7A above was obtained by positioning a transducer at 1 mm positions across a flow phantom in our laboratory. FIG. 10B illustrates the mapped PW Doppler image data or B mode image data that results or B mode data interlaced or otherwise combined with color flow Doppler measurements.

Figure 11A:
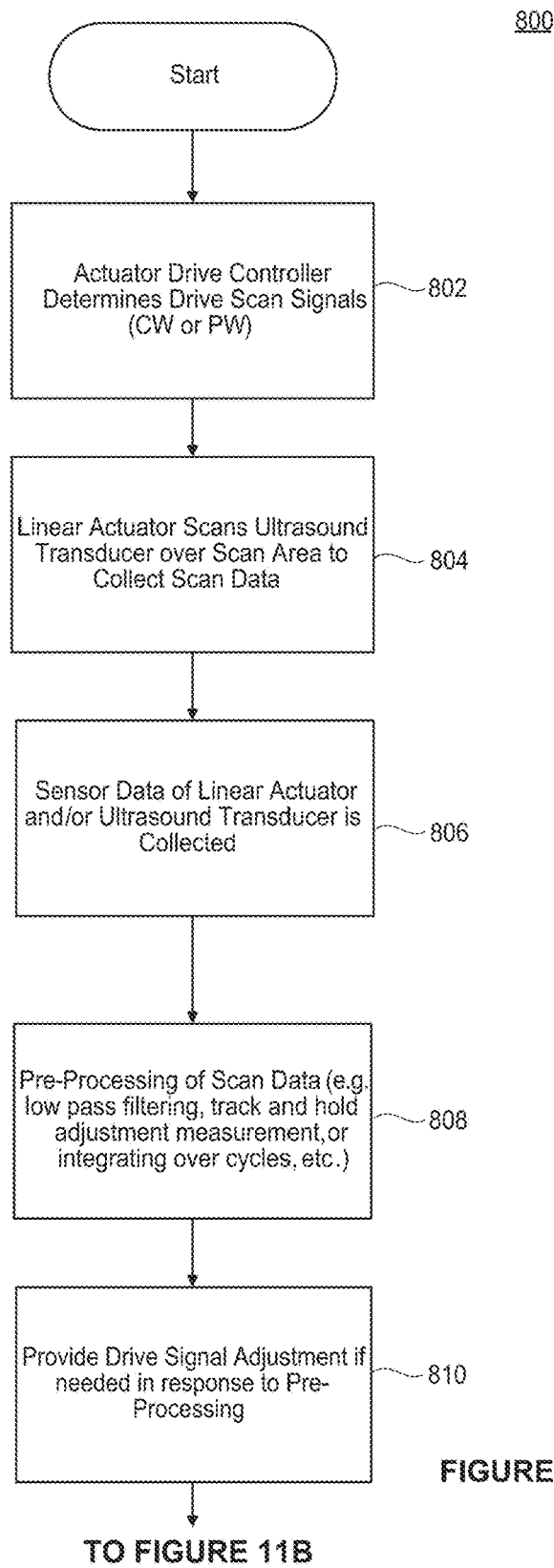

FIGS. 11A and 11B illustrate a diagram 800 for an ultrasound imaging system implemented in a "Doppler window" configuration. Initially, at a block 802, the actuator drive controller determines drive scan signals, e.g., for CW or PW Doppler scanning, and provides those to ultrasound transducer and the linear actuator. These drive scan signals will control linear actuation of the transducers along a path defined by the linear actuator. These drive signals may further include controls for scanning transducer elements along angular scan paths, during translation along the linear path. At a block 804, the linear actuator scans the ultrasound transducers over a scan area collecting scan data. In the illustrated example, at a block 806, the sensor is collected and the scan data and sensor data is provided to a feedback module for pre-processing. At a block 808, the feedback module pre-processing on the scan data and is able to determine whether further adjustments should be made to the drive signals, where based on that pre-processing, then adjustment signals are provided to the linear actuator control, at a block 810

In any event, the pre-processed scan data may be transmitted wirelessly to a remote imaging system, via block 812. At a block 814, the remote imaging system may perform various ultrasound imaging analysis, e.g., edge detection, decorrelation for 3D imaging, shear movement compensation/adjustment, wall shear velocity, wall shear rate, high resolution motion tracking, high resolution strain and strain rate or other derived parameters such as accumulated strain over few to may frames collected over time during ultrasound data acquisition. These clinically important parameters are often derived using partial derivatives in space and time of tissue location signals (i.e., RF speckle motion) and may be integrated with a variety of combinations (example: integrating strain rate signals over time to achieve strain). Once the remote imaging system has completed formation of the ultrasound image data, e.g., B mode image data, CW Doppler image data, PW Doppler image data, that image data is transmitted back to the scanning device, via a block 816, in an image format for ready display on a "Doppler window" or "ultrasound window" or "strain rate window" display mode of the device, by block 818. In this way, additional image processing is not needed for the display of the ultrasound data, thereby allowing for real-time display, in a streaming manner or a buffered manner, of the ultrasound images.

Figure 12:
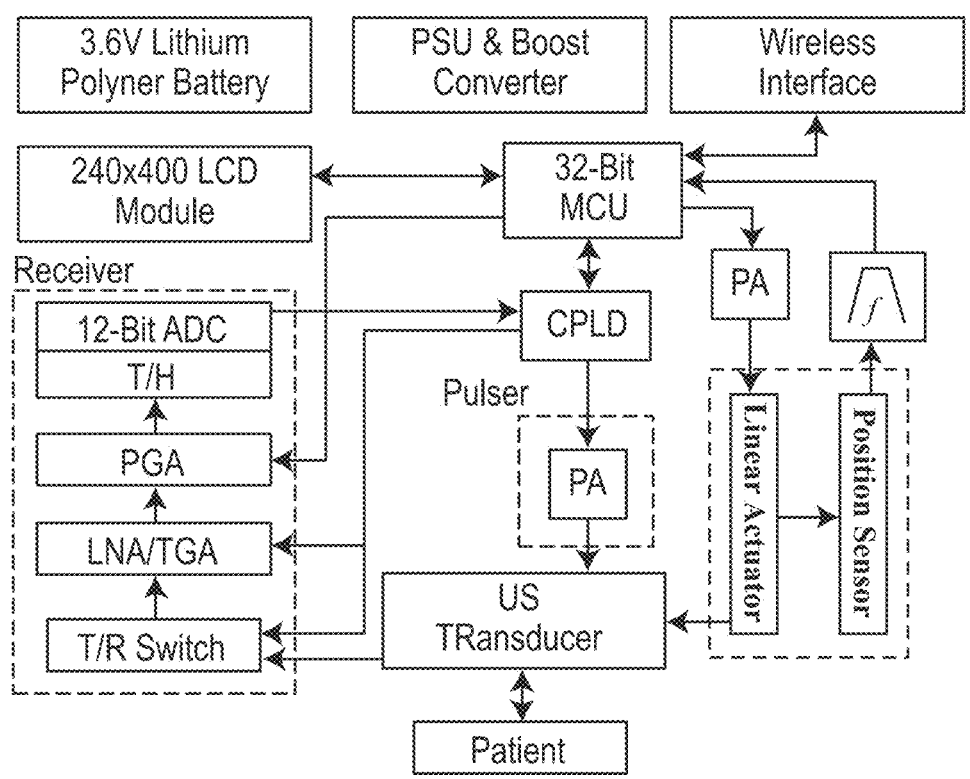
FIG. 12 is a system diagram of another example scanning device.

FIG. 12 illustrates another example scanning device 900. The device is similar to that of FIG. 8 in that processor (e.g., an 80 MHz 32-bit MIPS microcontroller (MCU)) manages communications, house-keeping and interfaces with a complex programmable logic device (CPLD) to perform ultrasound pulsing. The MCU is responsible for configuring the CPLD with the specific parameters necessary to create the required pulse-receive sequence, initiating the pulse/acquisition sequence, and reading the received RF data, for example, via an 8-bit data bus interface. The MCU also controls the linear drive actuator for scanning the ultrasound transducer and a position sensor supplying a feedback signal to a receiver module that performs bandpass signal filtering and a track and hold (T/H) noise reduction as part of a feedback close-loop control within the MCU. The MCU communicates the pre-processed ultrasound scan data, through a wireless link, to a remote imaging system that processes the data into an ultrasound image and communicates that ultrasound data back to the MCU for display on an LCD display. While no display is shown in the example of FIG. 8, it will be appreciated by persons skilled in the art that an LCD display will be incorporated into that design for display of remotely-processed ultrasound images, both B mode images and PW Doppler images, in a similar manner.

Indeed, an advantage of the techniques presented in this document is that by off-loading some or all the more complex ultrasound image processing to a remote imaging system, we are able to more effectively integrate the ultrasound transducer with a display, providing system designers with greater flexibility in where the ultrasound image can be displayed. In order to perform medical procedures, there is substantial advantage for the viewing screen to be in the field of view of the operator performing the procedure. The present techniques are able to overcome the bandwidth and processing limitations of conventional designs through the distributed architecture of image processing, where the display module may be located anywhere convenient for the physician including within the field of view of an operating physical at the point of a treatment on the body. In some examples, in fact, the ultrasound transducer and the display may be part of an integrated device, i.e., a contiguous device, not requiring external wiring or coupling between the probe and display. In this way, as the physician is treating a vessel, for example by introducing a needle or catheter into the vessel or other structure as part of a medical procedure, the physician can readily view, in real-time, the effects on the vessel by placing the display at the operation point of the treatment.

The present techniques may be used to assess CV disease, including carotid artery stenosis in high-risk groups. The position and degree of stenosis in the carotid artery is a known peripheral vascular ultrasound examination used to diagnose atherosclerosis, to determine associated stroke risk, and to determine who will benefit from endarterectomy or carotid endovascular procedures/stenting. The scanning devices herein may be used as part of carotid artery measurement system, determining, in an automated or semi-automated manner, user-independent measurements of carotid stenosis severity in a point-of-care setting, and in accordance with clinical consensus guidelines on carotid duplex stenosis measurement.

Figure 13:
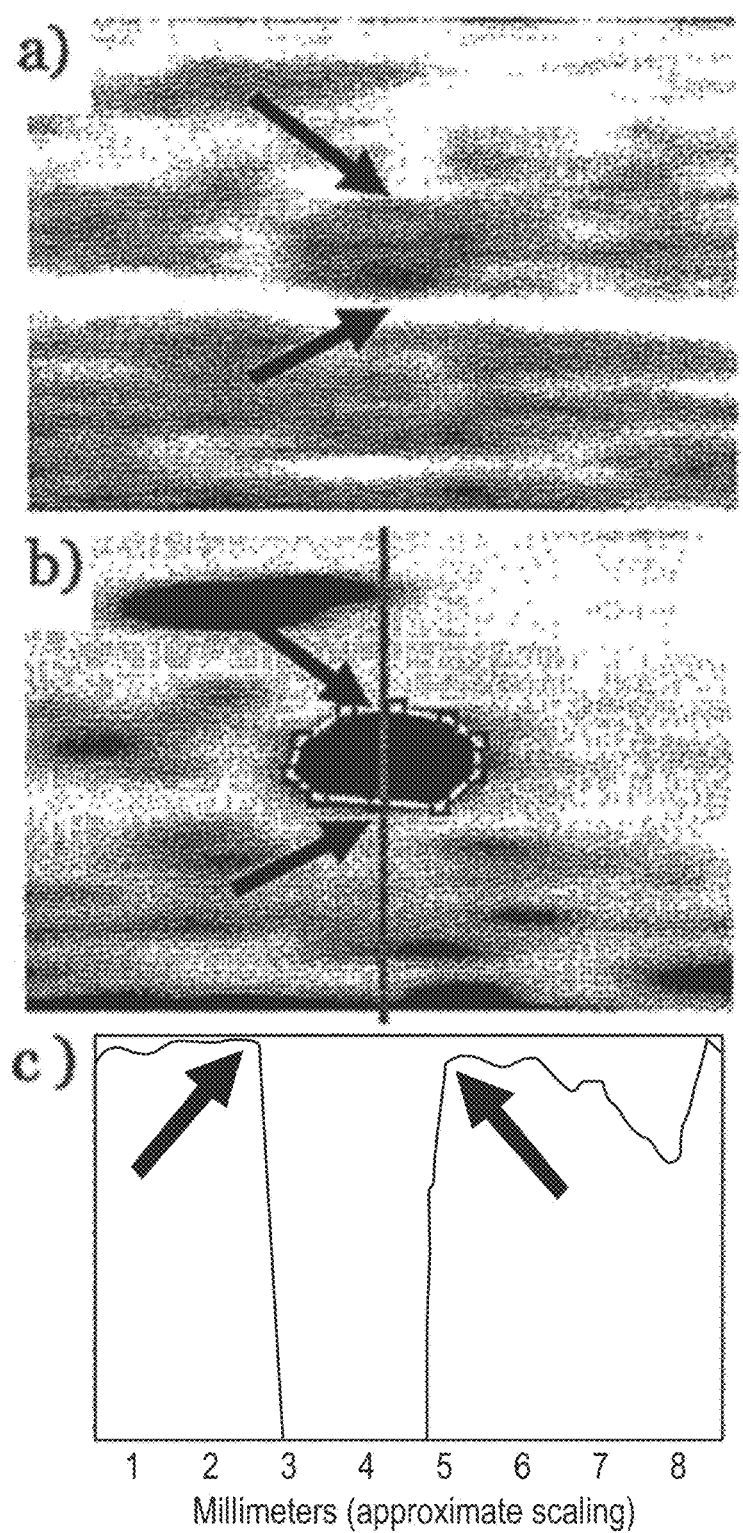
FIG. 13A is an image of a conventional B-scan image of the cross-section of a brachial artery.
FIG. 13B is an image of the map of the correlation function with increasing correlation in higher intensity as a result of using the PW Doppler imaging analysis techniques, in accordance with an example herein.
FIG. 13C is a plot showing the correlation function for a pair of frames along the centerline in FIG. 13B, demonstrating the high decorrelation gradient at the vessel edge, in accordance with an example.

For the example, in the process of FIG. 11, the remote imaging system can perform edge detection on the scan data to identify the inner and/or outer wall of the carotid artery, a valuable step for accurate quantitative analysis. For example, at the remote imaging system, the RF A-line data from the scanning device may be reassembled into a matrix describing the scan plane and correlated scan data from with previous frames. Soft tissue usually exhibits excellent frame-to-frame correlation; however the blood flow in arteries dramatically decreases the correlation in the regions of blood flow. FIG. 13A shows the conventional B-scan image of the cross section of a brachial artery. FIG. 13B, however, shows the map of the correlation function with increasing correlation in higher intensity as a result of using the PW Doppler imaging analysis, described hereinabove and in U.S. Pat. Nos. 6,167,765, 6,575,927, and 6709414. A decorrelation measurement is performed on the scan data, over multiple scan cycles, and results in the sharp contrast at the lumen boundary where blood flow causes correlation to decrease sharply. The centerline depicts the anticipated automated vessel center, where FIG. 13C shows the correlation function for a pair of frames along the centerline in FIG. 13B, demonstrating the high decorrelation gradient at the vessel edge.

The remote imaging system is configured to automatically identify the arterial vessel lumen by computing a binary mask and applying a threshold to the correlation map. If variability in the scan conditions prevents a static threshold (i.e. 80%) to be used, a fuzzy-logic based dynamically controlled threshold will be implemented using heuristics describing a "good" correlation map of a carotid artery. The resulting binary mask will be searched for regions where the carotid artery may be located. Based on the geometry, distensibility and size of the selected region, discrete tracking boxes will be automatically sized and placed appropriately. These boxes can be joined to trace an outline of the carotid artery.

Figure 14:
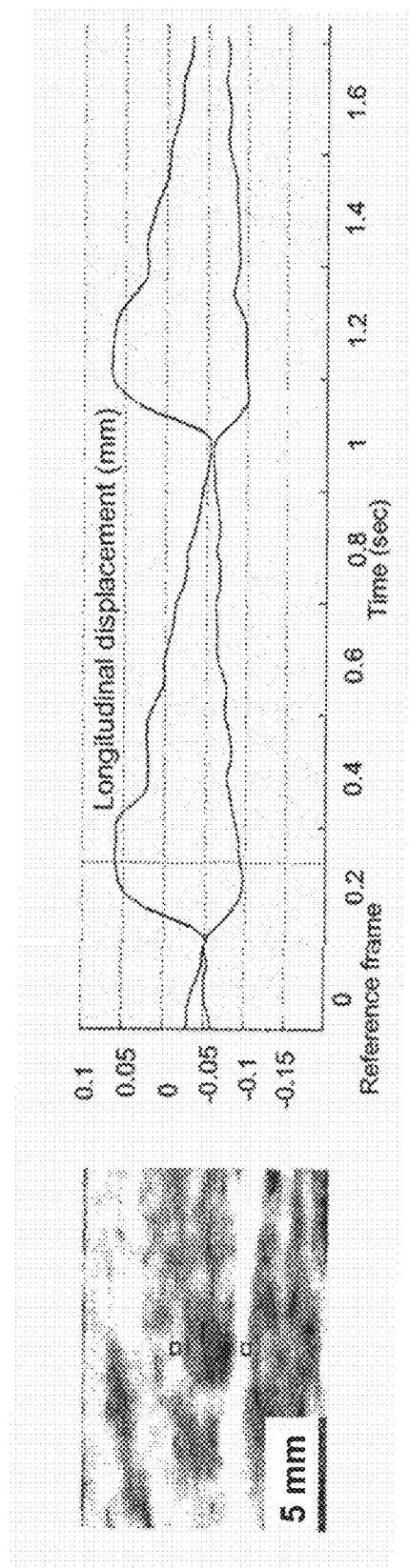
FIG. 14 is a plot showing spatial resolution for motion tracking.

FIG. 14 demonstrates that spatial resolution for motion tracking of approximately 0.01 mm is reasonable and reproducible between cardiac cycles. This resolution is more than adequate for measuring subtle changes in diameter required for carotid stenosis assessment and for distensibility measurements. The algorithm for the arterial wall detection will take into account the width of the kernel in optimizing edge detection. The artery diameter will also be measured building upon algorithms we have developed as depicted in FIG. 14, showing the accurate artery tracking during 2 cardiac cycles. FIG. 14 left shows the B-scan of an artery with blue the top line and bottom line tracking box above and below the artery lumen edge.

Figure 15:
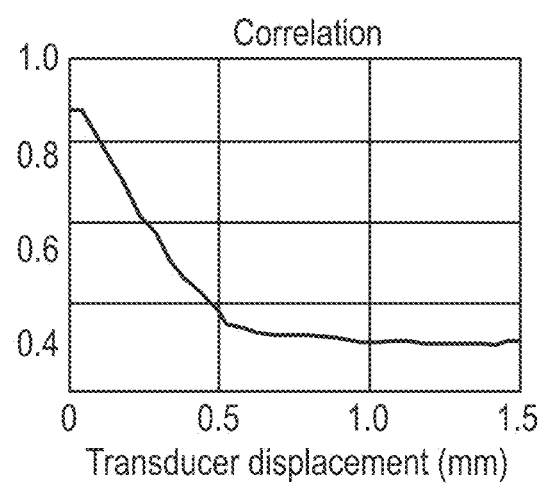
FIG. 15 is a plot of transducer displacement versus RF beam correlation.

In some examples, the remote imaging system will produce 3D ultrasound imaging. For 3D data acquisition, the remote imaging system with receive and store a series of 2D images. The ultrasound transducer will be moved during scan data capture so that the motion simulates clinical carotid scanning (slowly moving from the angle of the mandible to the sternal notch). We have tested the practice of RF signal tracking to estimate transducer motion and depending on beam geometry and frame rate, the simulations show that 10 Hz will allow accurate tracking of up to 1 cm per second. Because each nominally spaced 2 mm ultrasound frame slice will be imaged over one cardiac cycle (approximately one second; or frames), we anticipate very accurate transducer motion estimation at 5% of the maximal tracking velocity. In other examples, optical tracking and accelerometers may be used instead. The results in FIG. 15 show a high degree of confidence in our ability to use this method to accurately track, and coupled with the signal recognition strategies, to render the 3D image.

Figure 16:
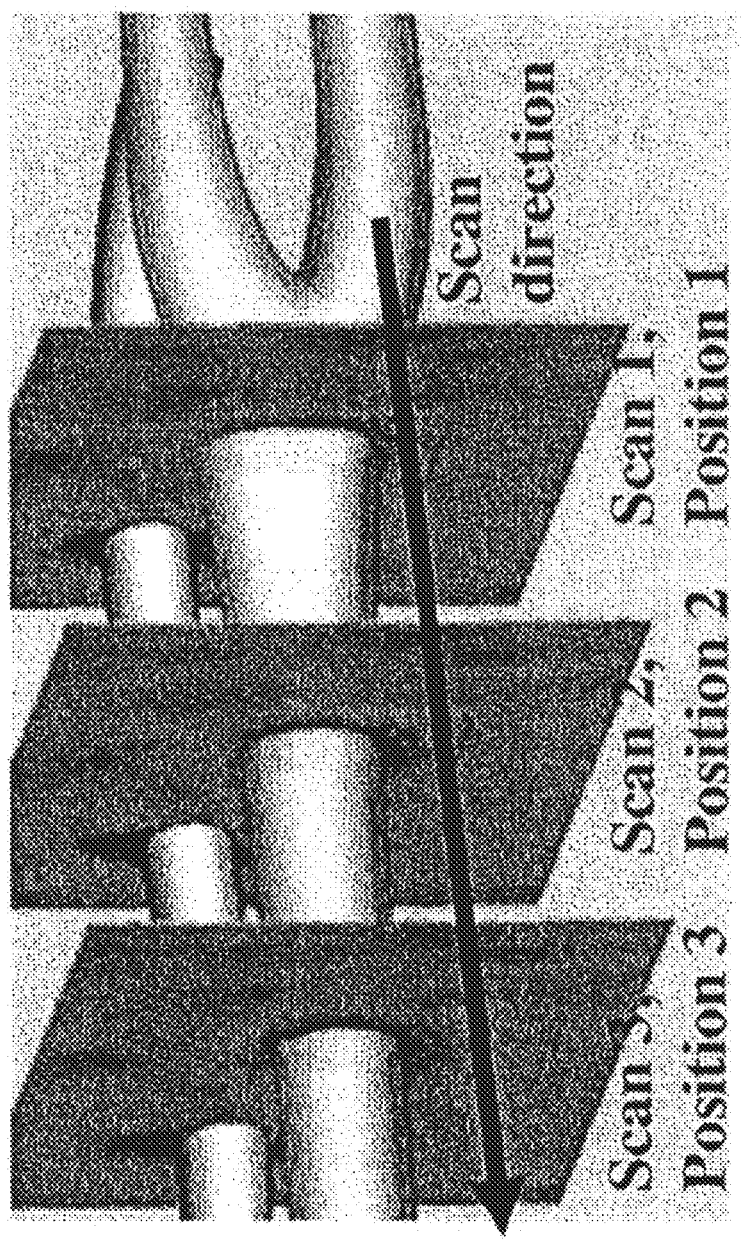
FIG. 16 is a depiction of a data acquisition technique using stacked images at different scan positions, in accordance with an example.

At the remote imaging system, each 2D plane will be assembled into a 3D data cube with descriptors indexing its temporal and spatial index. Correlation-based, phase-sensitive speckle tracking algorithm may be used to track tissue displacement. The scan plane belonging to a temporal set is subdivided into kernels that are shifted, multiplied and summed with the vectors from sequential planes from the same set to produce auto- and cross-correlation signals describing the temporal variation in tissue geometry. By combining the tracking boxes outlining the artery in each 2D B-scan slice, a 3D mesh of the artery geometry can be obtained. FIG. 16 shows the concept of data acquisition using stacked images from planar cross sections of duplex images stitched together into a 3D measurement field. Conventional Doppler blood flow velocity methods may also be used to detect regions of stenosis and to determine the blood flow profile over the vessel lumen for each B-scan slice over a cardiac cycle. Once the 3D representation of the vessel is obtained, angle correction of the Doppler profile will be performed, prior to the resulting 3D ultrasound image data being sent back to the scanning device "Doppler window".

In some examples it may be desirable to produce a transducer with a geometry that minimizes fluid drag. In order to optimize the mechanical motion of the magnetic drive device, the geometry of the moving transducer assembly may be particularly selected. As the transducer translates through the device, it experiences a force given by the Cauchy stress tensor σ integrated over the surface area of the transducer S.

$$F=\iint_S \sigma \cdot \hat{n} dS = \iint_S (-pI+\mu(\nabla u+\nabla u^T))\cdot \hat{n} dS$$

Figure 19:
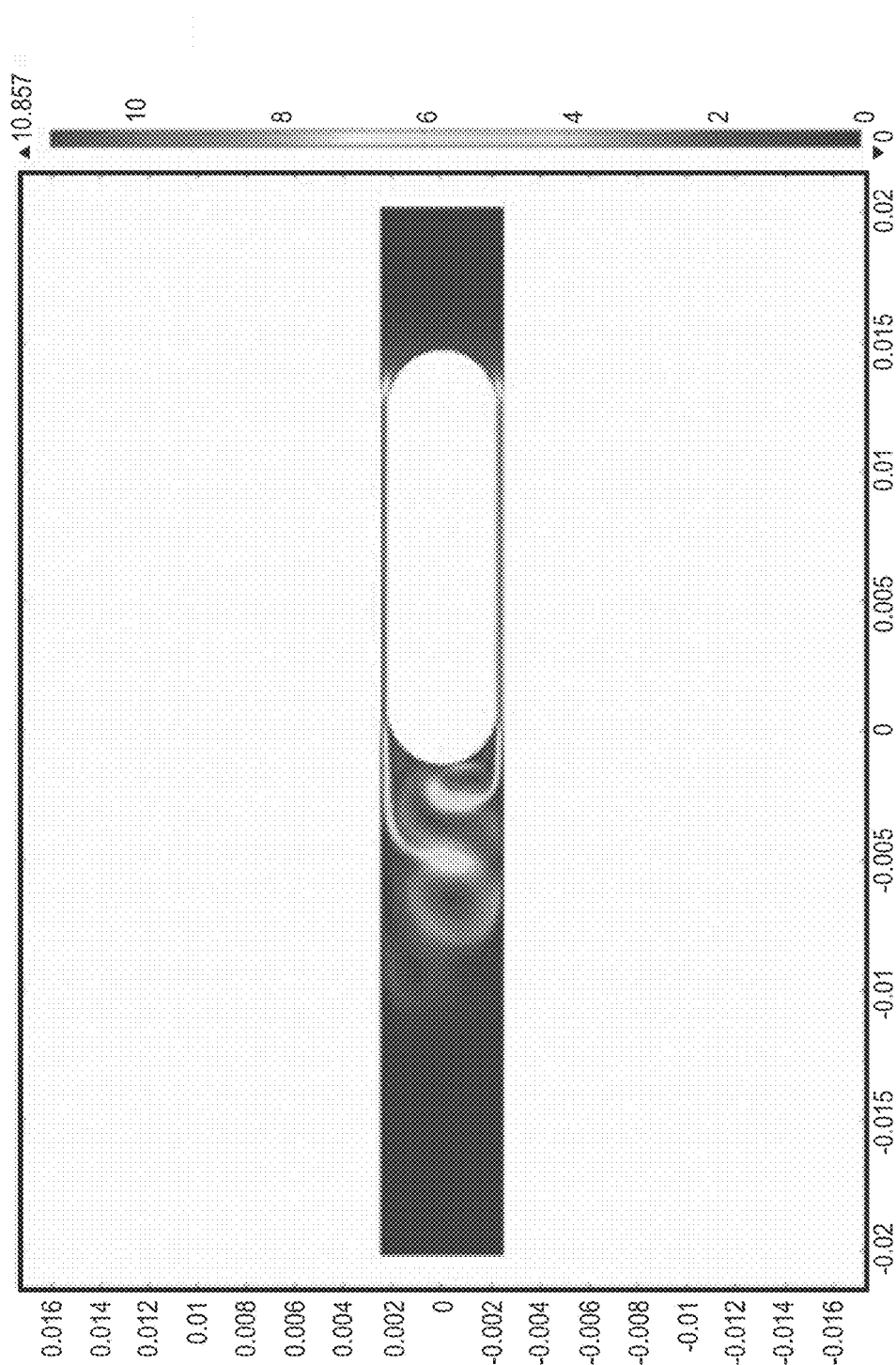
FIG. 19 is an illustration of flow dynamics during movement of a transducer assembly, in accordance with an example.

The pressure drag force is proportional to the unit normal component in the direction of the transducer motion. In order to minimize this component of the drag force, a transducer assembly with a geometry that minimizes this component of the unit normal may be chosen. And because the drag force is area dependent, it may also be desirable to minimize the surface area of the transducer. Further still, since the magnetic drive device enables imaging as the transducer moves both forward and backward, it may be desirable to have the transducer with a fore-aft symmetry. An example transducer profile is shown in FIG. 19.

Figure 20:
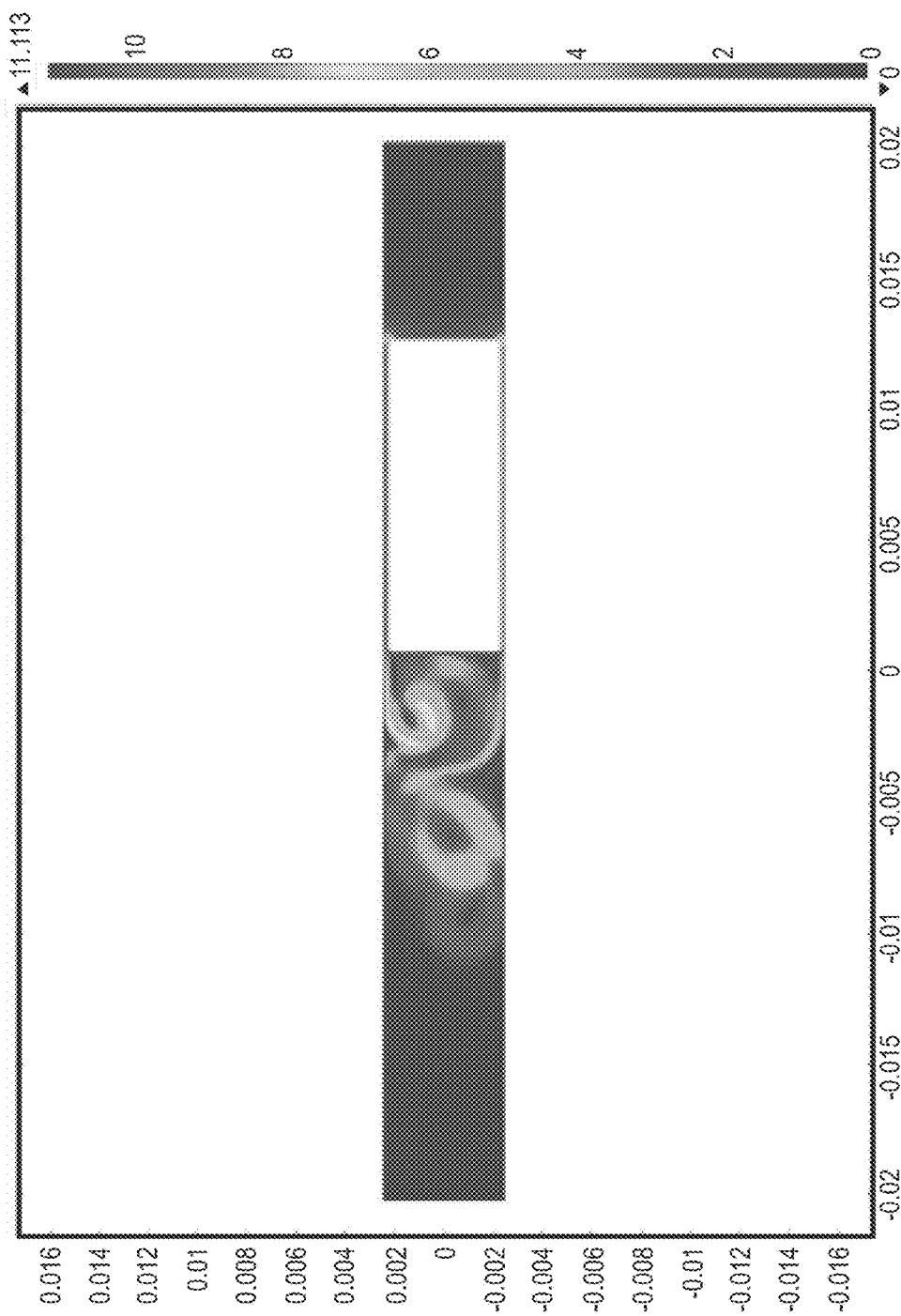
FIG. 20 is an illustration of flow dynamics during movement of a transducer assembly, in accordance with an example.

The presence of fluid dynamic instabilities is marked by a sudden deviation from given flow pattern, often as a result of a variation of a specific parameter. Often, this leads to the loss of a simple flow structure, such as the transition from laminar flow to turbulent flow. One instability that may affect some magnetic drive designs is the formation of vortex streets in the transducer wake. Computational fluid dynamics simulation results show that under expected operating conditions, these instabilities may form (see, FIG. 20). As the transducer moves through a coupling fluid, alternating vortices may be shed from the trailing edge. This results in both increased drag and a periodic lift force that may lead to unpredictable wobbling, thus reducing actuator accuracy. As such, it may be desirable to use a transducer that includes a geometry that minimizes features conducive to vortex shedding. In addition, it may be desirable that the transducer exhibit top-bottom symmetry or some degree of such symmetry.

Figure 21:
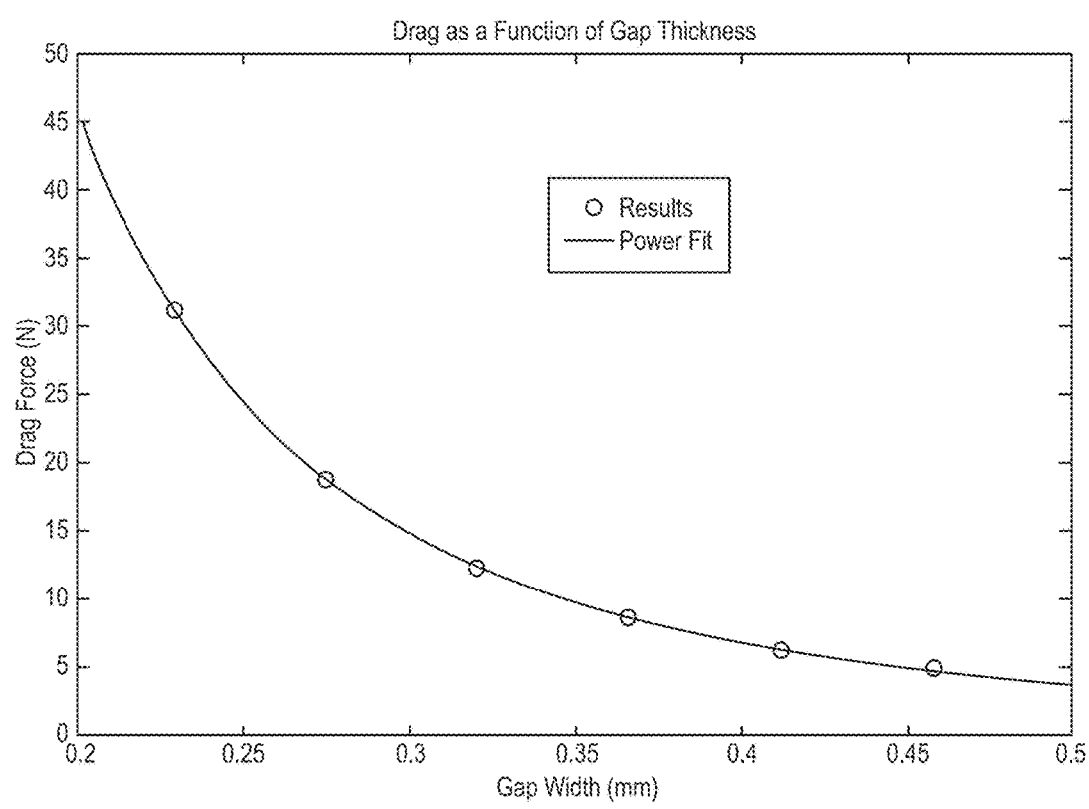
FIG. 21 is a plot drag force versus gap width for a transducer assembly, in accordance with an example.

The magnetic drive device housing geometry represents the outer boundary of the fluid flow field. Unsteady finite element analysis was used to show that narrow gaps between the transducer and the housing result in large velocity gradients and therefore high viscous drag on the transducer. The fluid drag is extremely sensitive to small changes in the gap size (see, FIG. 21). This allows a large degree of flexibility in decreasing fluid drag while still maintaining a small, portable device.

It may also be desirable to have a housing geometry with a clearance for the transducer large enough such that fluid drag is minimized while small enough that the onset of fluid instability is avoided.

From the Cauchy stress tensor σ, we find that the drag on an object moving through a viscous fluid increases with increasing viscosity. As such, in some examples, the coupling fluid viscosity should be minimized in order to minimize drag force on the transducer. At the same time, low fluid viscosity can increase the Reynolds number, thus increasing the chance of instability formation. Therefore, it may be desirable to use a transducer coupling fluid of high enough viscosity to suppress fluid instabilities but low enough viscosity to minimize fluid drag. In any event, any mechanical considerations should be balanced against the acoustic properties of the fluid in order to achieve the desired ultrasound signal quality.

While the techniques herein are described in particular example applications, such as Doppler ultrasound to visualize blood flow through a blood vessel like the carotid artery, it will be appreciated by persons skilled in the art, that these techniques may be extended to any number of 2D and 3D ultrasound imaging applications, including, but not limited to, bone sonography to diagnose osteoporosis, echocardiogram to view the heart, heart valves chambers and functional assessment of the heart by use of advanced tools such as strain and strain rate imaging, fetal and other obstetrical ultrasound such as locating the placenta, ultrasound-guided biopsies, Doppler fetal heart rate monitors, evaluating the echogenicity of any subsurface structure, surface or sub-surface ulceration, examination of muscles, tendons, other connective tissue, nerves, and bones, examination of internal abdominal organs such as but not limited to the kidney, liver, gallbladder. The techniques may be used for any number of applications directed to measuring and assessing a physiological condition, these include arterial applications, deep venous thrombosis, peripheral artery disease measurement, dialysis vascular access applications, and computationally intensive vascular modeling techniques.

Included also is the use of any of these devices in the "receive mode" for the gathering of ultrasound data in combination with any other means of generating the acoustic signal such and photo-acoustics or acoustic radiation force imaging (ARFI) techniques. Photo-acoustics generally refers to using photons (electromagnetic energy particles) to interact with subsurface structures in such a way as to cause the subsurface structure emit acoustic energy in response to being subjected to photons (electromagnetic energy). Typically, the stimulus (photons) is in the form narrow bandwidth light (wide range of frequencies used, not restricted to the visible or invisible spectrum) generated in the form of laser light shined on the region of the body to be examined and an ultrasound receiver is used to collect the ultrasound data to generate diagnostic information or imaging information for display to the user. ARFI uses a focused (spatially localized) acoustic impulse to cause subsurface force and motion or subsurface localized stress and resulting motion or motion gradient (strain) that can be tracked or detected by the devices described herein to perform measurements such as strain, strain rate, Doppler, motion detection, or correlation or decorrelation based measurements. These may be used to characterize subsurface tissues and structures in any of the exam procedures such as those outlined in [0067] above.

The "Doppler window" device can be particular useful in invasive treatment procedures, such as central venous catheter (CVC) insertion, peripheral inserted central catheters (PICCs) insertion, and peripheral intravenous (IV) catheters insertion. Doppler ultrasound may be used for placement determinations for any of these and other procedures to improve safety and decrease cannulation-related complication rates.

Furthermore, the techniques herein may be used to allow for distributed processing of any number of temporally and spatially derived information from repeated measurements in either (or both) time and over a spatial region (in one or more dimensions) to increase the diagnostic information obtained from this system. This includes time-integration (the integral or summation over time) of the velocity data to yield a displacement map over a region that is in real-time or has been previously obtained (for post processing of data). As examples, the spatial derivatives of these time-integrated displacement maps give the strain maps (strain tensors) and allow measurement of tissue mechanical properties. Combinations of partial derivatives of the (both or either) time and space distributions defined in an arbitrary (generalized) coordinate system yield the following information as examples: displacement, strain, normal and shear strain, strain rates (both normal and shear), and discontinuities or abrupt changes in any of these derived parameters give information about the mechanical properties of the imaged structures. These derived or combination values may be fit to models representing physical features of the anatomic region being imaged for increased utility of the diagnostic information derived from the imaged data. Of note, the partial spatial derivatives of a single image in time of the Doppler map gives the strain rate (normal and shear strain rate depending on the partial derivative), so this item includes derived information using a single point in time (more accurately from a single image from data collected over a brief time interval, i.e. one "frame" in common imaging parlance).

The various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism.

The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The invention claimed is:

1. An ultrasound scanning device for providing real-time two-dimensional scan data of a sample area, the scanning device comprising:

a magnetic drive assembly defining a first scanning direction of freedom for moving a scan head of the magnetic drive assembly along a curvilinear path, the magnetic drive assembly including a housing, the housing containing a fluid and maintaining the fluid within an area defined by a housing base and a housing cap;

a guide rail structure comprising a plurality of guide rails encapsulated by the housing, the guide rail structure defining the curvilinear path;

a plurality of fixed permanent magnets, each fixed permanent magnet of the plurality of permanent magnets magnetizing at least one guide rail of the plurality of guide rails and each fixed permanent magnet of the plurality of permanent magnets located outside the curvilinear path of the scan head; and the scan head of the magnetic drive assembly, the scan head encapsulated by the housing and positioned to move within the fluid in the housing and comprising a coil, an ultrasound transducer, and a position sensor, and the scan head moveable on the guide rail structure between the plurality of permanent magnets which are fixed relative to that movement and wherein the scan head is movable in response to drive signals provided to the magnetic drive assembly, the ultrasound transducer providing ultrasound scanning over a first scan plane corresponding to the sample area and extending below a surface contact area for the scanning device.

2. The ultrasound scanning device of claim 1, wherein the magnetic drive assembly defines a second scanning direction of freedom, different than the first scanning direction of freedom, to scan within the first scan plane.

3. The ultrasound scanning device of claim 1, wherein the ultrasound transducer defines a second scanning direction of freedom, different than the first scanning direction of freedom, to scan within the first scan plane.

4. The ultrasound scanning device of claim 2 or 3, wherein the second scanning direction of freedom is scanned electrically or mechanically.

5. The ultrasound scanning device of claim 4, a magnetic drive assembly controller is to scan the ultrasound transducer in the first scan plane to effect one of either Doppler velocity data, pulse-echo ultrasound data for radio-frequency tracking, or B mode data over the first scan plane.

6. The ultrasound scanning device of claim 1, wherein the magnetic drive assembly defines a second scanning direction of freedom, different than the first scanning direction of freedom, to scan within a second plane, different from the first scan plane for obtaining three-dimensional scan data.

7. The ultrasound scanning device of claim 1, wherein the ultrasound transducer defines a second scanning direction of freedom, different than the first scanning direction of freedom, to scan within a second plane, different from the first scan plane for obtaining three-dimensional scan data.

8. The scanning device of claim 1, wherein the magnetic drive assembly comprises two fixed permanent magnets positioned on opposite sides of the guide rail structure and having opposing poles.

9. The scanning device of claim 8, wherein at least another guide rail of the plurality of guide rails is a passive guide rail, wherein the passive guide rail provides support and is not magnetized by the plurality of fixed permanent magnets.

10. The scanning device of claim 1, wherein the ultrasound transducer is a piezoelectric transducer.

11. The scanning device of claim 1, wherein the ultrasound transducer is a Capacitive Micromachined Ultrasonic Transducers (CMUT) transducer.

12. The scanning device of claim 1, wherein the ultrasound transducer is a single element transducer.

13. The scanning device of claim 1, wherein the ultrasound transducer is a multiple-element transducer, wherein each of a plurality of elements is aligned along the curvilinear path during scanning.

14. The scanning device of claim 1, wherein the ultrasound transducer is mounted on a swivel base of the scan head or another base having a second scanning direction of freedom different than the first scanning direction of freedom, such that the ultrasound transducer is aligned for scanning along the curvilinear path during scanning and has an orientation that changes in response to the swivel base or another base to scan at different angles during scanning along the curvilinear path, wherein the orientation changes are either actively induced or passively induced.

15. The scanning device of claim 1, wherein a sensor of a magnetic drive assembly controller determines position and orientation of the ultrasound transducer.

16. The scanning device of claim 1, wherein a sensor of a magnetic drive assembly controller determines position by sensing a physical characteristic of the ultrasound transducer or the magnetic drive assembly.

17. The scanning device of claim 16, wherein the physical characteristic is a physical alteration in the magnetic drive assembly performance resulting from scanning the ultrasound transducer.

18. The scanning device of claim 16, wherein the physical characteristic is a coordinate of the ultrasound transducer or the magnetic drive assembly.

19. The scanning device of claim 16, wherein the physical characteristic is a force generated by the ultrasound transducer or the magnetic drive assembly, a velocity of the scanning of the ultrasound transducer, or an acceleration of the scanning of the ultrasound transducer.

20. The scanning device of claim 1, wherein a sensor of a magnetic drive assembly controller determines position by sensing an electrical signal characteristic of the ultrasound transducer or the magnetic drive assembly.

21. The scanning device of claim 20, wherein the electrical signal characteristic is one or more of a drive current supplied to the magnetic drive assembly, a drive voltage supplied to the magnetic drive assembly, a voltage differential signal for the magnetic drive assembly, signal strength required to the ultrasound transducer during scanning, and optical encoder information.

22. The scanning device of claim 1, wherein a magnetic drive controller employs a rule-based control scheme.

23. The scanning device of claim 1, wherein a magnetic drive controller employs a velocity control scheme.

24. The scanning device of claim 1, wherein a magnetic drive controller employs a positioning control scheme.

25. The scanning device of claim 1, wherein a magnetic drive controller employs a frame rate control scheme.

26. The scanning device of claim 1, wherein a magnetic drive controller employs one or more of a proportional-integral-derivative feedback control scheme, a pole placement control scheme, a sliding mode control scheme, an adaptive control through recursive least squares parameter estimation scheme, a Luenberger observer scheme, a Kalman filter scheme, an extended Kalman filter scheme, and an unscented Kalman filter scheme.

27. The scanning device of claim 1, wherein a magnetic drive controller includes a feedback control for ultrasound transducer positioning.

28. The scanning device of claim 27, wherein the feedback control comprises a sample and hold controller for compensating against operator movement of the scanning device during operation.

29. The scanning device of claim 28, wherein the sample and hold controller compensates against operator movement using an edge integrity algorithm.

30. The scanning device of claim 28, wherein the sample and hold controller provides real-time self registration of the two-dimensional scan data.

31. The scanning device of claim 1, wherein the scanning device is a low-profile wearable device.

32. The scanning device of claim 1, wherein the scanning device is a low-profile wrist mountable wearable device.

33. The scanning device of claim 1, wherein a controller of the magnetic drive assembly further utilizes sensed data supplied from the ultrasound transducer to provide a control for the drive signals sent to the magnetic drive assembly.

* * * * *